United States Patent [19]

Chen

[11] Patent Number: 5,259,939

[45] Date of Patent: Nov. 9, 1993

[54] CAPILLARY ELECTROPHORESIS BUFFER

[75] Inventor: Fu-Tai A. Chen, Brea, Calif.

[73] Assignee: Beckman Instruments, Inc., Fullerton, Calif.

[21] Appl. No.: 753,279

[22] Filed: Aug. 30, 1991

[51] Int. Cl.$^5$ .................... G01N 27/26; G01N 27/447
[52] U.S. Cl. ............................ 204/180.1; 204/299 R
[58] Field of Search ........................ 204/299 R, 180.1

[56] References Cited

U.S. PATENT DOCUMENTS

| | | | |
|---|---|---|---|
| 4,680,201 | 7/1987 | Hjerten | 204/299 R X |
| 4,931,328 | 6/1990 | Swedberg | 204/299 R X |
| 5,006,313 | 4/1991 | Swedberg | 204/299 R X |
| 5,089,103 | 2/1992 | Swedberg | 204/299 R X |
| 5,120,413 | 6/1992 | Chen et al. | 204/180.1 |

FOREIGN PATENT DOCUMENTS

| | | |
|---|---|---|
| 0442315A1 | 8/1991 | European Pat. Off. |
| 8912225 | 12/1989 | PCT Int'l Appl. |

OTHER PUBLICATIONS

Sally A. Swedberg "Characterization of Protein Behavior in High-Performance Capillary Electrophoresis Using a Novel Capillary System" Analytical Biochemistry 185, 51–56.

Abstract—Accession No. 54-10F00170, Bio Techniques, 10(5), May 1991, Mazzeo, J. R., et al: "Coated capillaries and additives for the separation of proteins by capillary zone electrophoresis and capillary isoelectric focusing", pp. 638–640, 642–645.

Abstract—Accession No. 54-10B00091, J. Chromatogr., 559(1-2), 18 Oct. 1991, Salomon, K., et al: "Evaluation of fundamental properties of a silica capillary used for capillary electrophoresis", pp. 69–80.

Jorgenson, J. W. and Lukacs, K. D. "Capillary Zone Electrophoresis." *Science* 222:266–272 (1983).

Hjerten, S. "High Performance Electrophoresis Elimination of Electroendosmosis and Solute Adsorption." *J. Chrom.*, 347:191–198 (1985).

Cobb, K. A. et al. "Electrophoretic Separations of Proteins in Capillaries with Hydrolytically Stable Surface Structures." *Anal. Chem.* 62:2478–2483 (1990).

Swedberg, S. A. "Characterization of Protein Behavior in High-Performance Capillary Electrophoresis Using a Novel Capillary System." *Anal. Biochem* 185:51–56 (1990).

Lauer, H. H. and McManigill, D. "Capillary Zone Electrophoresis of Proteins in Untreated Fused Silica Tubing." Anal. Chem. 58: 166–170 (1986).

Chen, Fu-Tai A. et al. "Capillary Electrophoresis-A New Clinical Tool." *Clin. Chem.* 7711:14–19 (1991).

Green, N. S. and Jorgenson, J. W. "Minimizing Adsorption of Proteins on Fused Silica in Capillary Zone Electrophoresis by the Addition of Alkali Metal Salts to the Buffers." *J. Chrom.* 478:63–70 (1989).

Bushey, M. M. & Jorgenson, J. W. "Capillary Electrophoresis of Proteins in Buffers Containing High Salt Concentrations of zwitterionic salts." *J. Chrom.* 480:301–310 (1989).

McCormick, R. M. "Capillary Zone Electrophoretic Separation of Peptides and Proteins Using Low pH buffers in Modified Silica Capillaries." *Anal. Chem.* 60:2322–2328 (1988).

Lauer, H. H. and McManigill, D. Trends *Anal. Chem.* 5:11 (1986).

Mitsyuk, B. M. "Mechanism of the Reaction of Silica with Phosphoric Acid in Aqueous Solutions." *Russian Journal of Inorganic Chemistry*, 17(4):471–473 (1972).

Emerick, R. J. "Phosphate Inhibition of Protein—Polysilicic Acid Complex Formation in Vitro: A Factor in Preventing Silica Urolithiasis." *J. Nutr.*, 117:1924–1928 (1967).

*Primary Examiner*—John Niebling
*Assistant Examiner*—John S. Starsiak
*Attorney, Agent, or Firm*—William H. May; P. R. Harder; Janis C. Henry

[57] ABSTRACT

Disclosed herein is a dynamic coating buffer useful in the analysis of samples by open-tube capillary electrtophoretic methods using untreated fused silica capillary columns. The dynamic coating buffer comprises at least one agent having at least two dissociation constants, and high ionic strength characteristics, said agent having a molarity range of from about 0.2M and about 1.0M and a pH range of from between about 3.0 and 11.0. A particularly preferred dynamic coating buffer comprises 0.5M sodium phosphate.

10 Claims, 25 Drawing Sheets

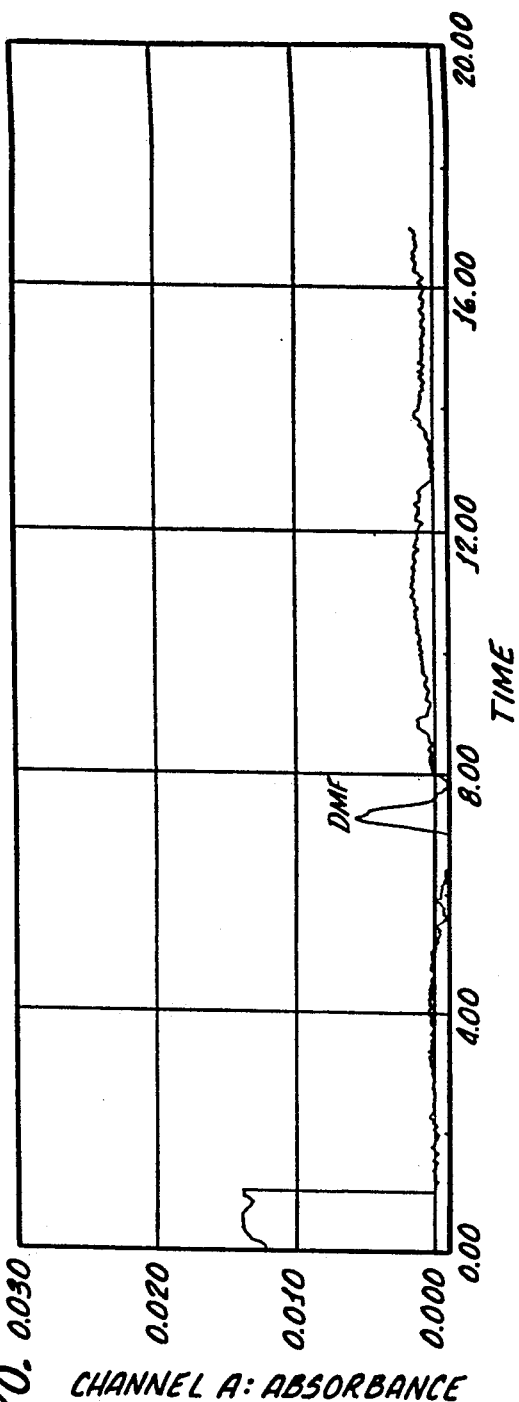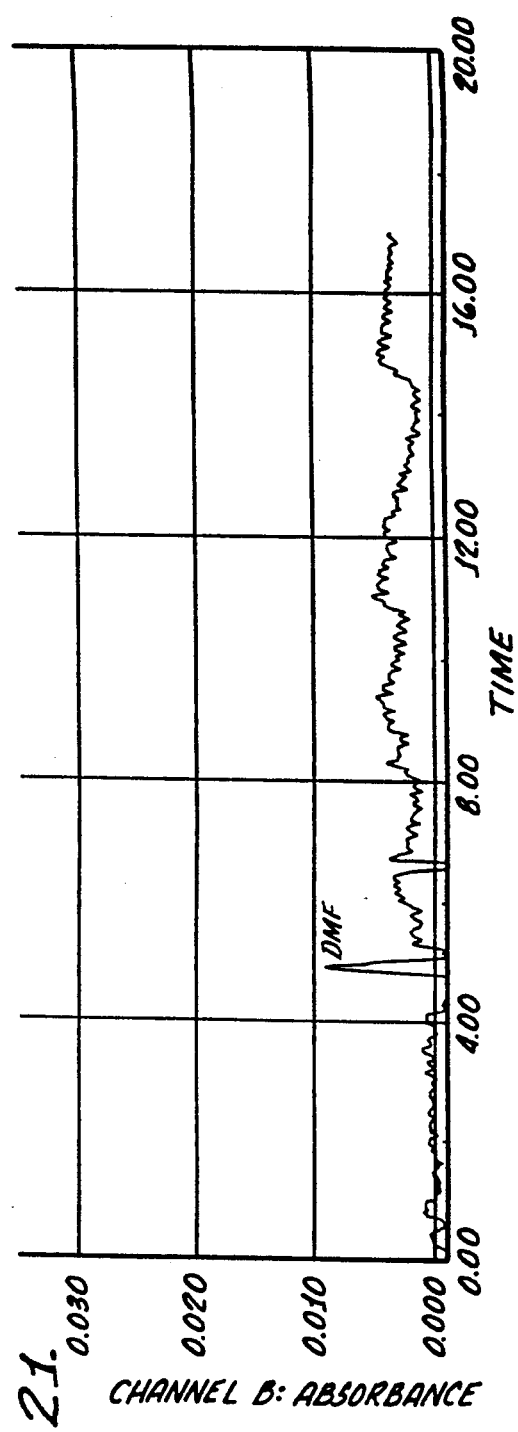

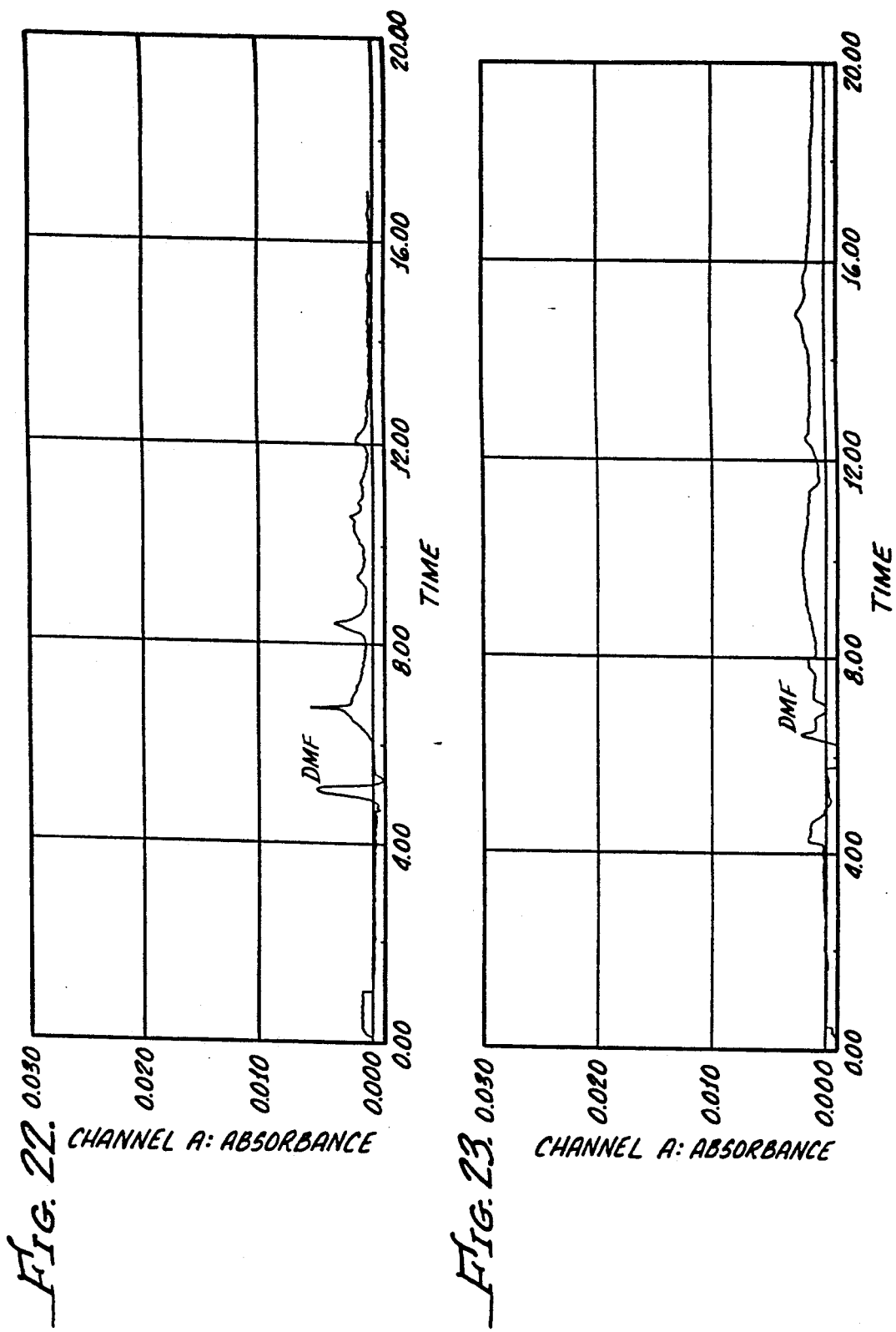

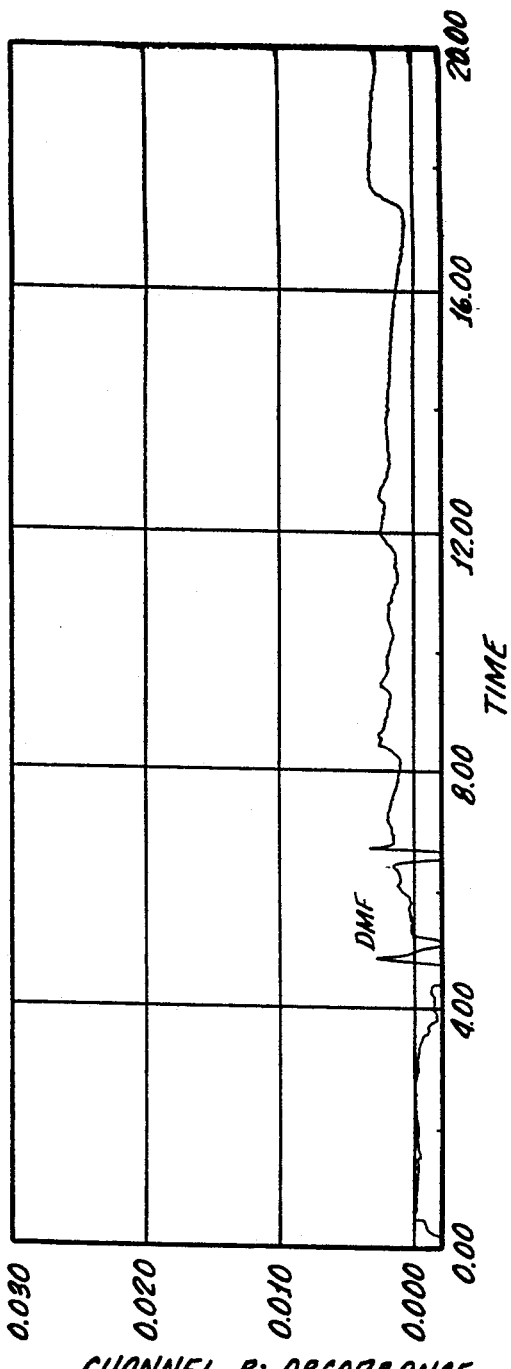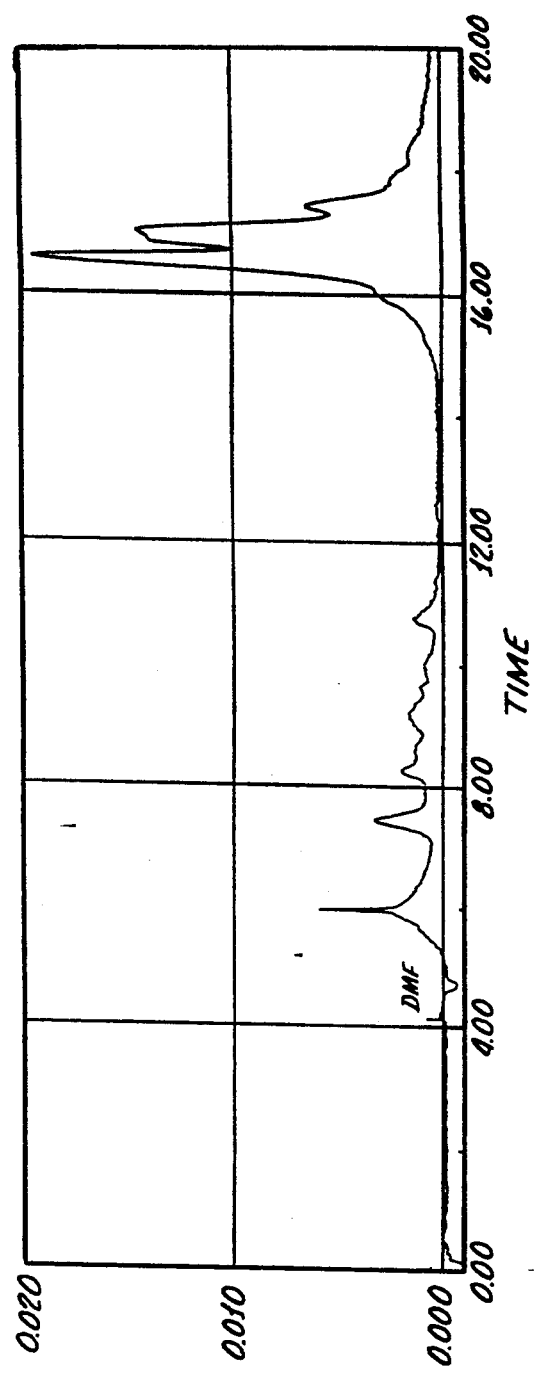

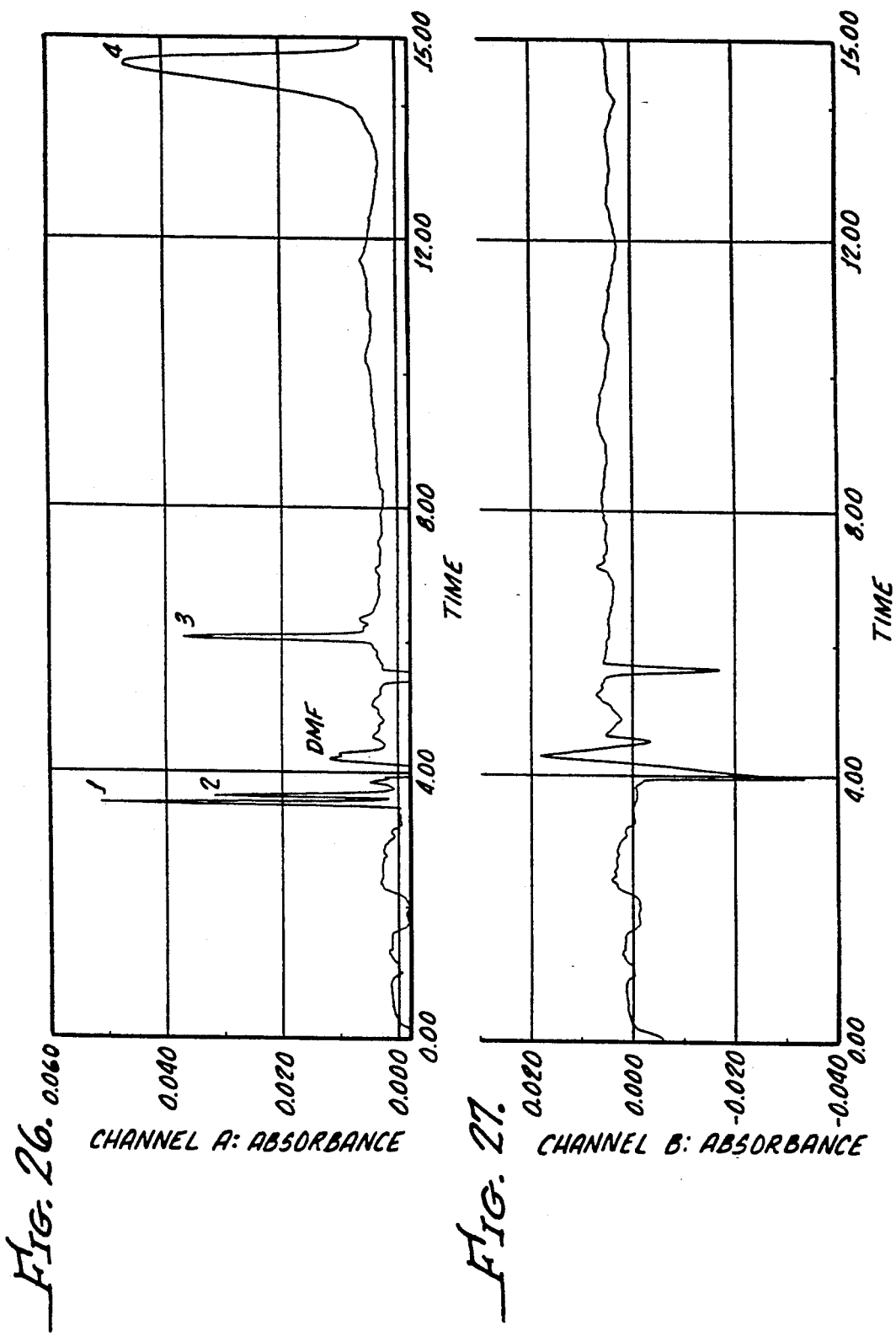

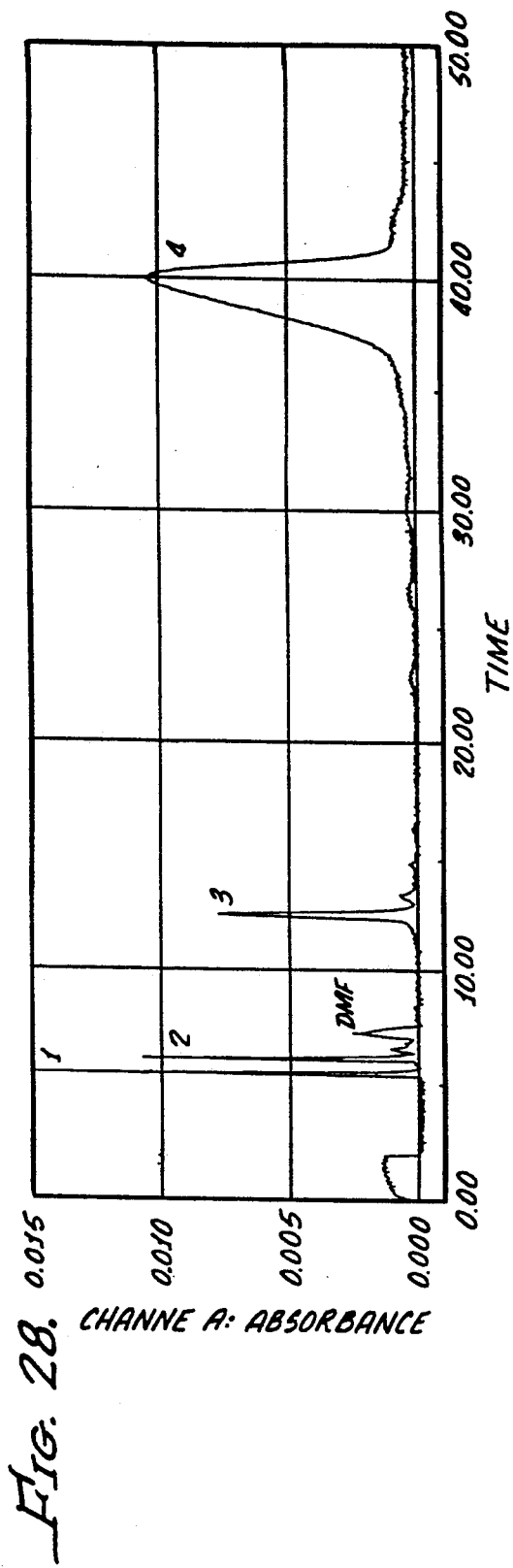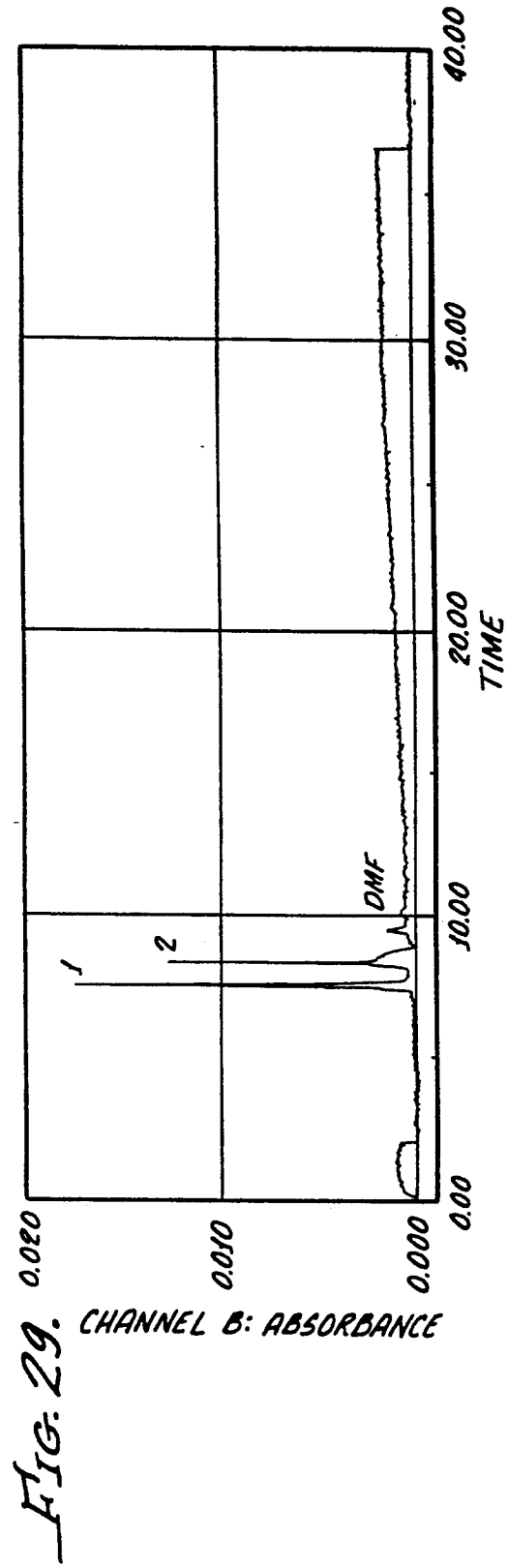
Fig. 28. CHANNEL A: ABSORBANCE
Fig. 29. CHANNEL B: ABSORBANCE

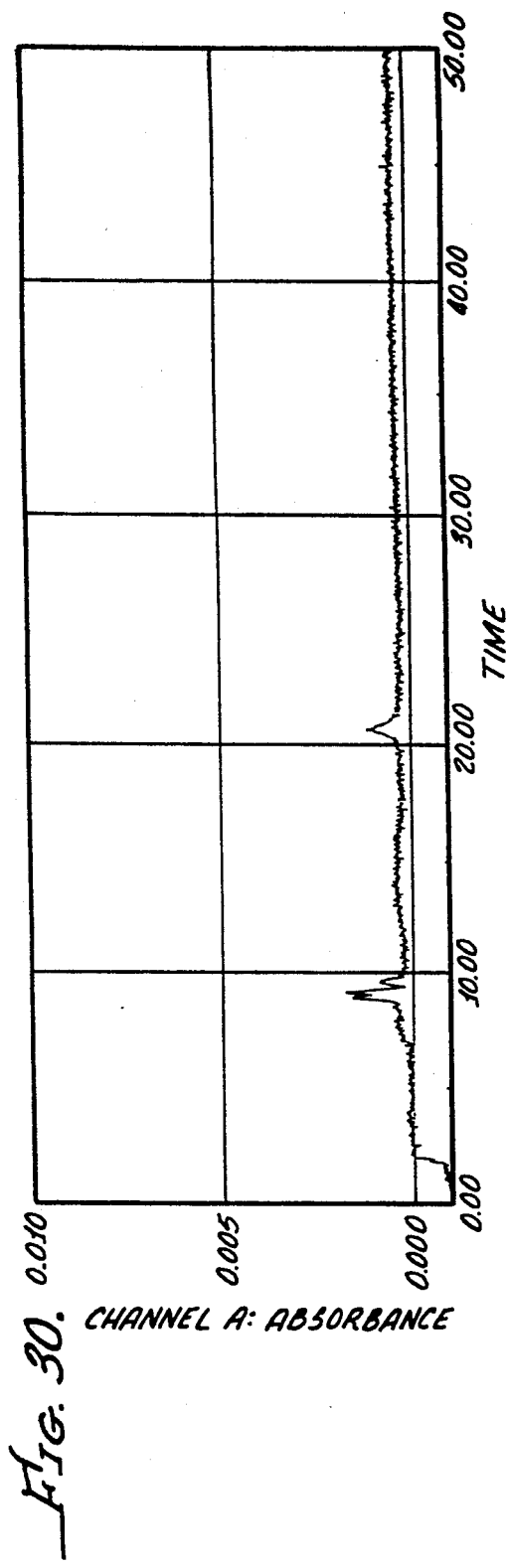
Fig. 30. CHANNEL A: ABSORBANCE
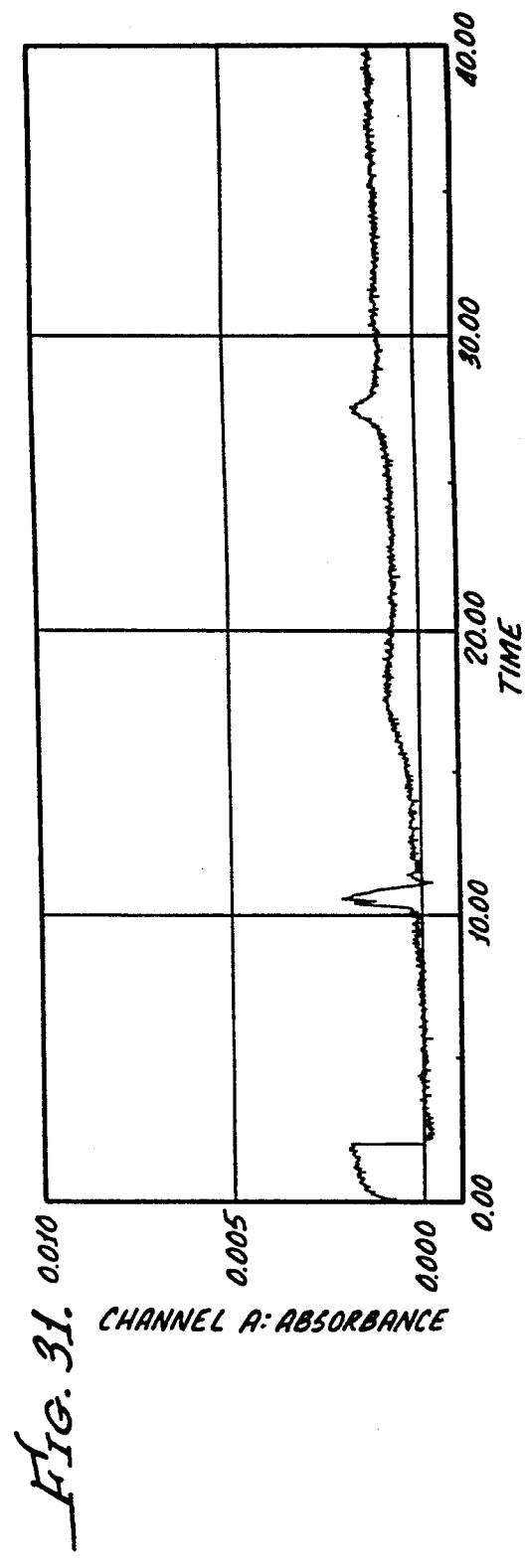
Fig. 31. CHANNEL A: ABSORBANCE

CAPILLARY ELECTROPHORESIS BUFFER

FIELD OF THE INVENTION

The preset invention is related to analysis of samples in general, analysis by capillary zone electrophoresis in particular, and specifically to dynamic coating buffers useful in open capillary zone electrophoresis.

BACKGROUND OF THE INVENTION

The articles set forth in the Background of the Invention are incorporated herein by reference.

Capillary zone electrophoresis ("CZE") is a technique which permits rapid and efficient separations of charged substances. In general, CZE involves introduction of a sample into a capillary tube, i.e. a tube having an internal diameter from about 5 to about 2000 microns, and the application of an electric field to the tube. The electric potential of the field both pulls the sample through the tube and separates it into its constituent parts. Each constituent of the sample has its own individual electrophoretic mobility; those having greater mobility travel through the capillary tube faster than those with slower mobility. As a result, the constituents of the sample are resolved into discrete zones in the capillary tube during their migration through the tube. An on-line detector can be used to continuously monitor the separation and provide data as to the various constituents based upon the discrete zones.

CZE can be generally separated into two categories based upon the contents of the capillary columns. In "gel" CZE, the capillary tube is filled with a suitable gel, e.g., polyacrylamide gel. Separation of the constituents in the sample is predicated in part by the size and charge of the constituents travelling through the gel matrix. In "open" CZE, the capillary tube is filled with an electrically conductive buffer solution. Upon ionization of the capillary, the negatively charged capillary wall will attract a layer of positive ions from the buffer. As these ions flow towards the cathode, under the influence of the electrical potential, the bulk solution (the buffer solution and the sample being analyzed), must also flow in this direction to maintain electroneutrality. This electroendosmatic flow provides a fixed velocity component which drives both neutral species and ionic species, regardless of charge, towards the cathode. The buffer in open CZE is as stable against conduction and diffusion as the gels utilized in gel CZE. Accordingly, separations can be obtained in open CZE quite similar to those obtained in gel-based CZE.

Fused silica is principally utilized as the material for the capillary tube because it can withstand the relatively high voltage used in CZE, and because the inner walls of a fused silica capillary ionize to create the negative charge which causes the desired electrosomatic flow. The ionization of the inner walls of the capillary tube, however, creates problems with respect to separation of proteinaceous materials. Proteins are hetero-polyelectrolytes (i.e. an approximate equivalent number of positively and negatively charged moieties within the molecule while the molecule itself has a neutral-charge). Thus, when ionized, a protein species can have a net positive charge distribution such that the protein species will adsorb quite strongly onto the ionized inner wall. This adsorption leads to artificial zone broadening in CZE, resulting in inconclusive, erroneous or incomprehensible results.

The pH of the electrolyte buffer can dramatically effect the efficiencies and resolutions of separation by CZE. Even a small shift in pH can have a large impact on the separation. With untreated fused silica capillary columns, however, this fact is a double edged sword because pH's other than near-neutral lead to the formation of negatively charged silanol groups on the inner wall of the capillary. Thus, heretofore, untreated fused silica capillary columns could not be used with a wide range of pH values.

One proposed attempt at solving this problem was to treat, or "coat", the inner wall of the capillary tube so that electrosomatic flow would be reduced when voltage was applied. That would, in turn, reduce adsorption of proteins onto the tube. Glycol modified fused silica capillaries have been used for serum protein analysis, but only with limited success. See Jorgenson, J. W. & Lukacs, K. D. "Capillary Zone Electrophoresis." *Science* 222:266-272 (1983). U.S. Pat. No. 4,680,201 describes coated capillary tubes comprising a bifunctional compound having a first functional group covalently attached to the wall and a second functional group capable of being polymerized. See also, Hjerten, S. "High-Performance Electrophoresis Elimination of Electrophoresis and Solute Adsorption." *J. Chrom.* 547:191-198 (1985) and Cobb, K. A. et al "Electrophoretic Separations of Proteins in Capillaries with Hydrolytically Stable Surface Structures." *Anal. Chem.* 62:2478-2483 (1990). Other covalently attached coatings are described in U.S. Pat. No. 4,931,328 and PCT Published Application No. WO 89/12225. See also, Swedberg, S. A. "Characterization of Protein Behavior in High-Performance Capillary Electrophoresis Using a Novel Capillary System." *Anal. Biochem.* 185:57-56(1990) (hereinafter "Swedberg").

Concomitantly, coated fused silica capillaries have a relatively short shelf-life and their coatings have a tendency to "dissolve" in an unpredictable manner. The aura of unpredictability is unacceptable in any environment where multiple samples will be analyzed on a frequent basis. Aside from the practical limitations with coated capillary columns, the associated costs also make them impractical. A coated capillary column applicable to commercially available CZE analyzers costs approximately $90.00 (United States of America. Of this amount, approximately $1.00 (United States of America) is attributed to the cost of the fused silica capillary itself. Thus, the major cost of such commercially available columns is related to the coating itself. On average, coated columns will begin to deteriorate after about 50 to 100 runs. As such, they are expensive to use.

Another proposed solution to the problem of protein adsorption was to use a buffer having a pH greater than the isoelectric points (pI) of the protein components of the sample. As is well known, when the pH is equal to the pI, the positive and negative moieties of the molecule are balanced. Similarly, when the pH is greater than pI, the negative moieties predominate and when the pH is less than the pI, the positive moieties exceed the negative moieties. For example, the pI of albumin is 4.6; therefore, at pH 4.6, the negatively charged and positively charged moieties of albumin are equally distributed on the surface of the albumin molecule and its overall charge is neutral. However, as the pH is raised above the isoelectric point, the negatively charged moieties predominate and the net charge is negative. Thus, under the influence of a high pH buffer, all of the protein species of the sample will have a negative charge and will be repelled from the negatively charged wall. This will, in turn, avoid or at least greatly diminish, their surface adsorption. However, large pH-pI differences can cause structural changes in the protein, or even hydrolysis. Attempts to electrophorese complex mixtures such as, e.g. human serum protein, in untreated fused-silica capillary tubes using buffer solutions having pH ranges from 5-8 have resulted in irreproducible migration of all sample zones. See Lauer, H. H. and McManigill, D. "Capillary Zone Electrophoresis of Proteins in Untreated Fused Silica Tubing." *Anal. Chem*, 58:166-169 (1986).

It has been theorized that protein adsorption onto the untreated fused capillary wall is due to ion exchange interactions between cationic sites in the protein and silicate moieties in the wall. See Jorgenson, J. W. "Capillary Electrophoresis", Chpt. 13, *New Direction in Electrophoretic Methods*. ACS Symp. Ser. 335, 1987 (Jorgenson, J. W. & Phillips, M., Eds.). Accordingly, it has been suggested to use high salt buffer conditions to reduce protein adsorption. See Lauer, H. H. & McManigill, D., *Trends Anal. Chem*. 5:11 (1986). However, increasing the salt concentration of the buffer has the effect of increasing the conductivity of the capillary tube which can dramatically increase the heat inside the tube. Increasing temperature causes the migrating zones to become diffused, thus decreasing resolution of the zones. In order to avoid such heat build-up, the electric potential applied to the capillary tube must be greatly diminished. This, however, has the undesirable effect of increasing the time necessary for analysis of the sample.

Alkali metal salts have been added to buffers in an effort to minimize protein absorption on fused-silica capillary tubes. Green, N. S. and Jorgenson, J. W. "Minimizing Adsorption of Proteins on Fused Silica in Capillary Zone Electrophoresis by the Addition of Alkali Metal Salts to the Buffers." *J. Chrom.* 478:63-70(1989) (hereinafter "Green"). Addition of $KS_2SO_4$ to a pH 9.0 buffer was reported to evidence little adsorption of two proteins which ordinarily demonstrate significant adsorption in a pH 9.0 buffer (lysozyme and trypsinogen). Similarly, zwitterionic salts have been added to such buffers. Busey, M. M. and Jorgenson, J. W. "Capillary Electrophoresis of Proteins in Buffers Containing High Concentrations of Zwitterionic Salts." *J. Chrom*. 480:301-310 (1989).

None of the preceding methodologies are sufficient for separating sample constituents over a wide range of pH values, i.e. about pH 3.0 to about pH 11.0. This is particularly highlighted in the untreated (i.e. non-coated) columns. As noted, each constituent of the sample to be separated has a unique isoelectric point. Thus, if the pH of the buffer is, e.g., 7.0, and the isoelectric points of two constituent samples are, e.g., 2.0 and 4.0, respectively, the resulting electropherogram may not evidence distinction between the two constituents. This is because the pH of the buffer may not allow for their proper separation, thus leading to co-migration of the two constituents which would appear as a single peak on an electropherogram.

Use of different buffer systems having different pH values has the undesirable effect of adding multiple variables to the analysis. I.e, an acidic pH (less than about 4.0) buffer may "interact" with the sample constituents in a manner differently than an alkaline pH buffer (greater than about 8.0). Ideally, a single buffer systems capable of having a range of pH values should be utilized such that any internal variability is negated.

Present coated capillary columns cannot withstand the rigors of buffers having the types of pH ranges noted above, i.e. from about pH 3.0 to about pH 11.0, due to the inherent unpredictability and instability thereof. Untreated columns avoid this problem, but have inherent problems with respect to sample constituent adsorption. What is needed, then, is a CZE buffer applicable over a range of pH values, which can be used in conjunction with open-tube CZE, and which substantially diminishes sample-constituent adsorption onto untreated capillary tubes.

SUMMARY OF THE INVENTION

The present invention satisfies the above need by providing a dynamic coating buffer useful in the CZE analysis of proteins, peptides and enzymes. As used herein, a "dynamic coating buffer" is a pH buffer solution comprising at least one agent capable of chemically reacting with an untreated fused silica tube and physically interacting via solvation with at least one ionized sample constituent, and having the following characteristics: (1) at least two dissociation constants ("pKa") and (2) high ionic strength. As used herein, the term "solvation" means that the agent and a sample constituent physically interact such that the two molecules behave as one, without chemically reacting in such a manner that the agent alters or otherwise changes the chemical characteristics of the constituent; "dissociation constant" or, pKa, means a pH at which the agent fully loses one proton; and "high ionic strength" means that the agent has a molarity of at least 0.2M.

Examples of suitable agents which may be used singularly or in combination in the dynamic coating buffer include phosphoric acid ($H_3PO_4$), alkali-metal phosphates having at least one proton, mono-, di-, tri-, and tetra-alkyl ammonium phosphate having from about 1 to about 8 carbon atoms, alkyl phosphate having from about 1 to about 20 carbon atoms, carbonic acid ($H_2CO_3$), alkali-metal carbonates having at least one proton, mono-, di-, tri-, and tetra-alkyl ammonium carbonate having from about 1 to about 8 carbon atoms, and alkyl carbonate having from about 1 to about 20 carbon atoms.

The dynamic coating buffer may also include acetic acid, 2-(N-morpholino) ethanesulfonic acid, 3-(N-morpholino) proponesulfonic acid, N-[tris-hydroxymethyl) ethyl] glycine, tris-(hydroxymethyl) aminomethane, cyclohexyl aminoethane - sulfonic acid, triethyl amine, dimethyl amine, alkyl amides having up to about 12 carbon atoms, N-2-hydroxyethyl piperazine-N'-3-propane sulfonic acid, piperazine-N, N'-bis (2-ethanesulfonic acid), 3-{[tris-(hydroxymethyl) methyl] amino} propanesulfonic acid, 2-{[(hydroxymethyl)methyl] amino} ethanesulfonic acid, and urea.

Preferably, the molarity range of the agent is between about 0.2M and about 1.0M, more preferably between about 0.4M and about 0.6M, and most preferably about 0.5M. The temperature range for CZE analysis is preferably conducted at between about 4° C. to about 60° C., and most preferably at about ambient (room) temperature. The pH range of the dynamic coating buffer is preferably between about 3.0 to about 11.0.

In a particularly preferred embodiment, the dynamic coating buffer comprises, in combination as needed, 0.5M of mono-sodium phosphate, 0.5M di-sodium phosphate and 0.5M tri-sodium phosphate, depending on the desired pH of the buffer. I.e., if the desired pH of the buffer is between about 4.0 and about 9.0, aliquots of $NaH_2PO_4$ and $Na_2HPO_4$ are admixed to achieve the pH value; if the desired pH of the buffer is greater than about 9.0, aliquots of $Na_2PHO_4$ and $Na_3PO_4$ are admixed to achieve the pH value.

BRIEF DESCRIPTION OF THE DRAWINGS

FIG. 20 is an electropherogram of serum proteins using a comparative buffer;

FIG. 21 is an electropherogram of serum proteins using a comparative buffer;

FIG. 22 is an electropherogram of serum proteins using a comparative buffer;

FIG. 23 is an electropherogram of serum proteins using a comparative buffer;

FIG. 24 is an electropherogram of serum proteins using a comparative buffer;

FIG. 25 is an electropherogram of serum proteins using a comparative buffer;

FIG. 26 is an electropherogram of Set A Model Proteins using a comparative buffer;

FIG. 27 is an electropherogram of serum proteins using the conditions of FIG. 26;

FIG. 28 is an electropherogram of Set A Model Proteins using a coated column and comparative buffer, pH 6.0;

FIG. 29 is an electropherogram of Set A Model Proteins using the conditions of FIG. 28, pH 7.0;

FIG. 30 is an electropherogram of serum proteins using the conditions of FIG. 28; and FIG. 31 is an electropherogram of serum proteins using the conditions of FIG. 29.

DETAILED DESCRIPTION OF PREFERRED EMBODIMENTS

Figure 1:
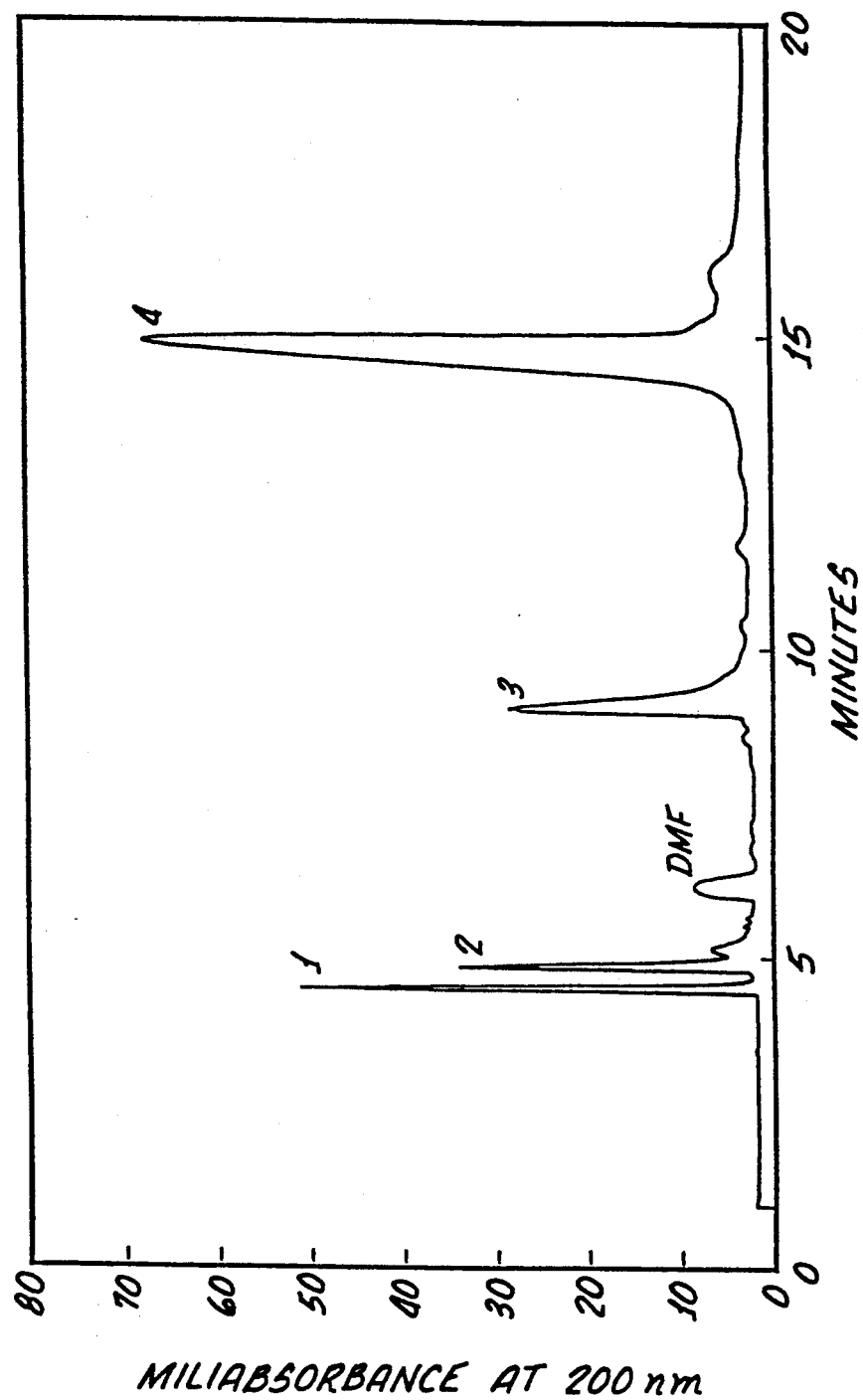
FIG. 1 is an electropherogram of four model proteins and a neutral marker (DMF) in dynamic coating buffer, pH 5.0.
Figure 2:
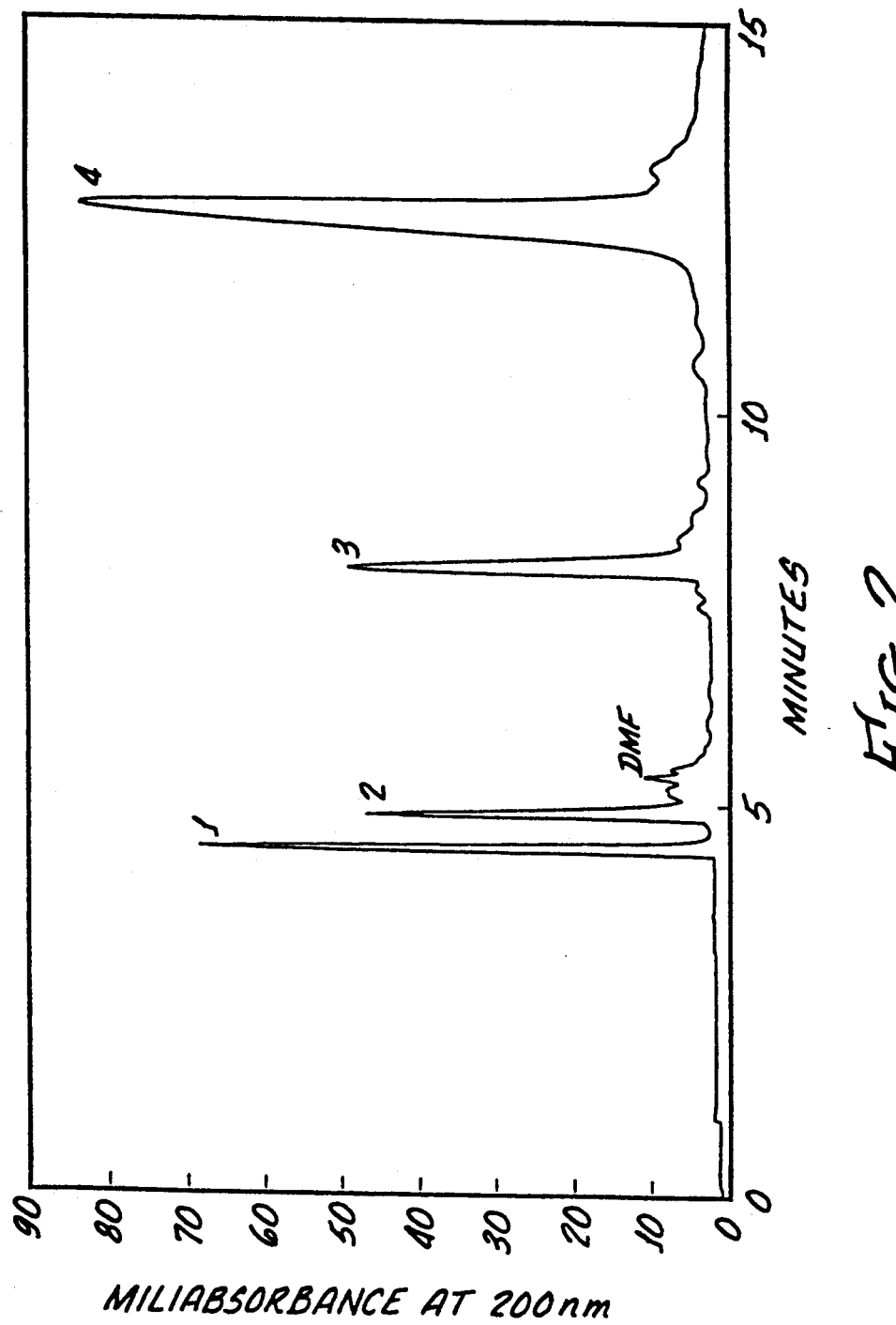
FIG. 2 is an electropherogram of the four model proteins and marker of FIG. 1 in dynamic coating buffer, pH 6.0.
Figure 3:
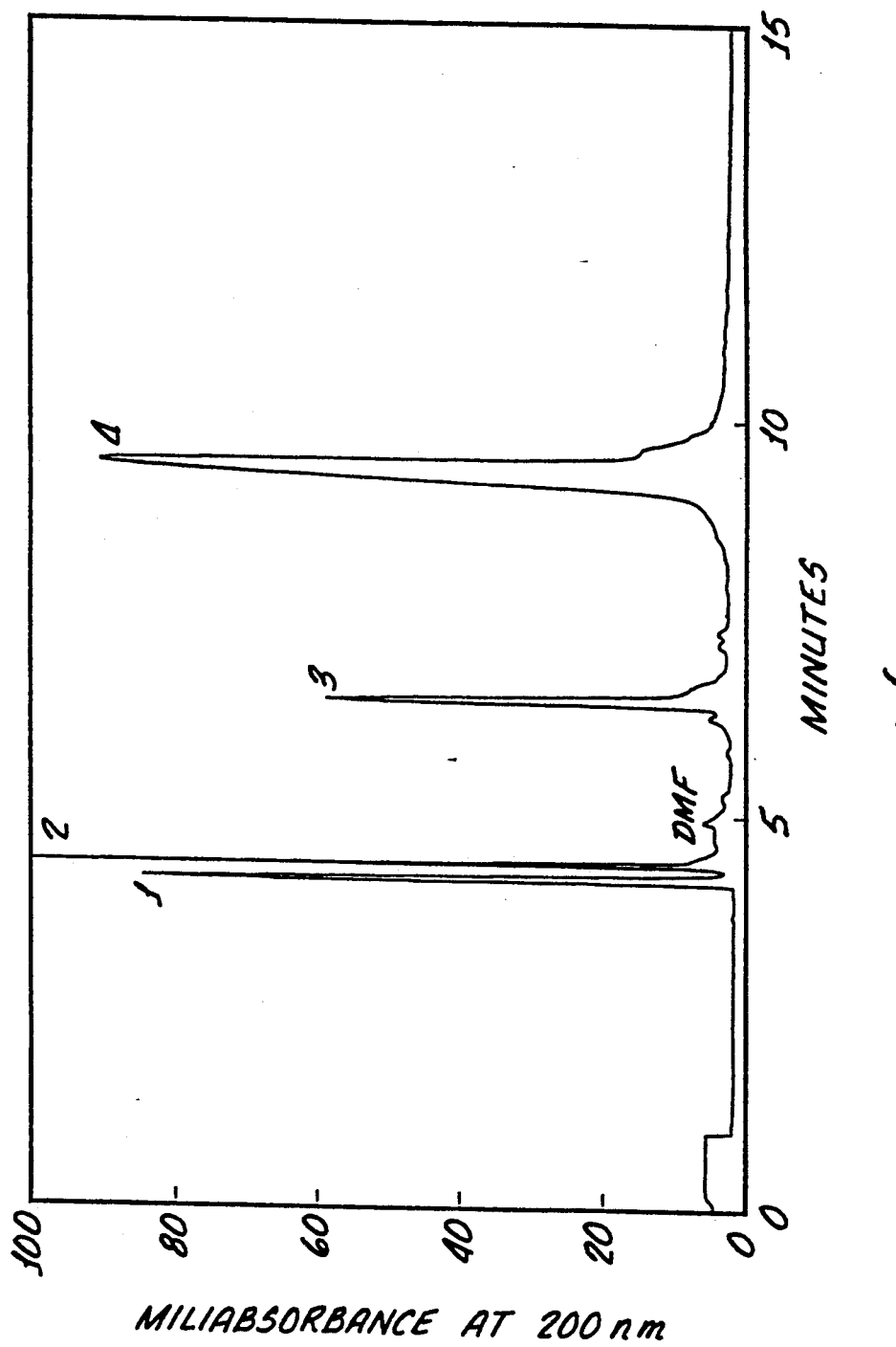
FIG. 3 is an electropherogram of the four model proteins and marker of FIG. 1 in dynamic coating buffer, pH 7.0.
Figure 4:
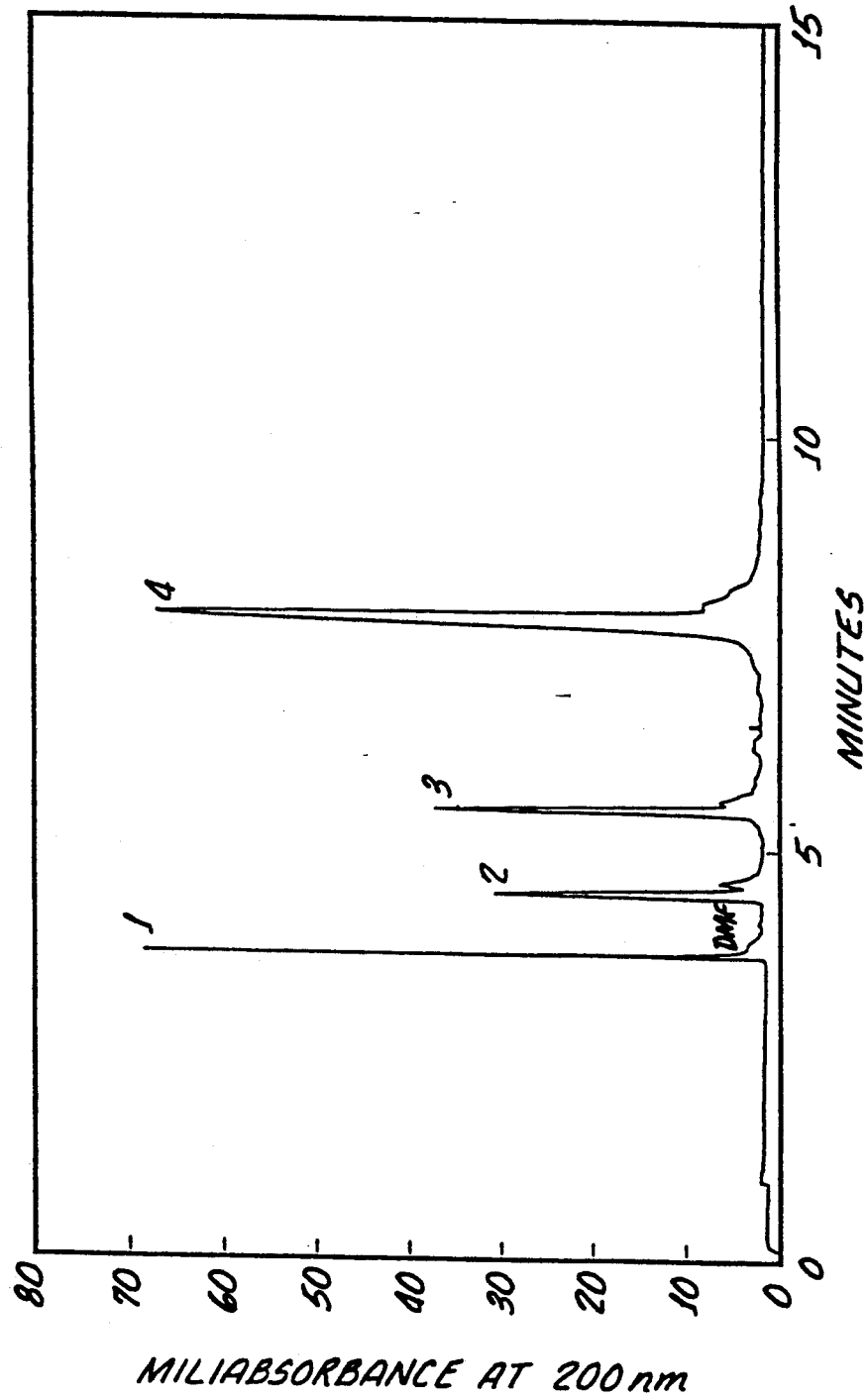
FIG. 4 is an electropherogram of the four model proteins and marker of FIG. 1 in dynamic coating buffer, pH 9.0.
Figure 5:
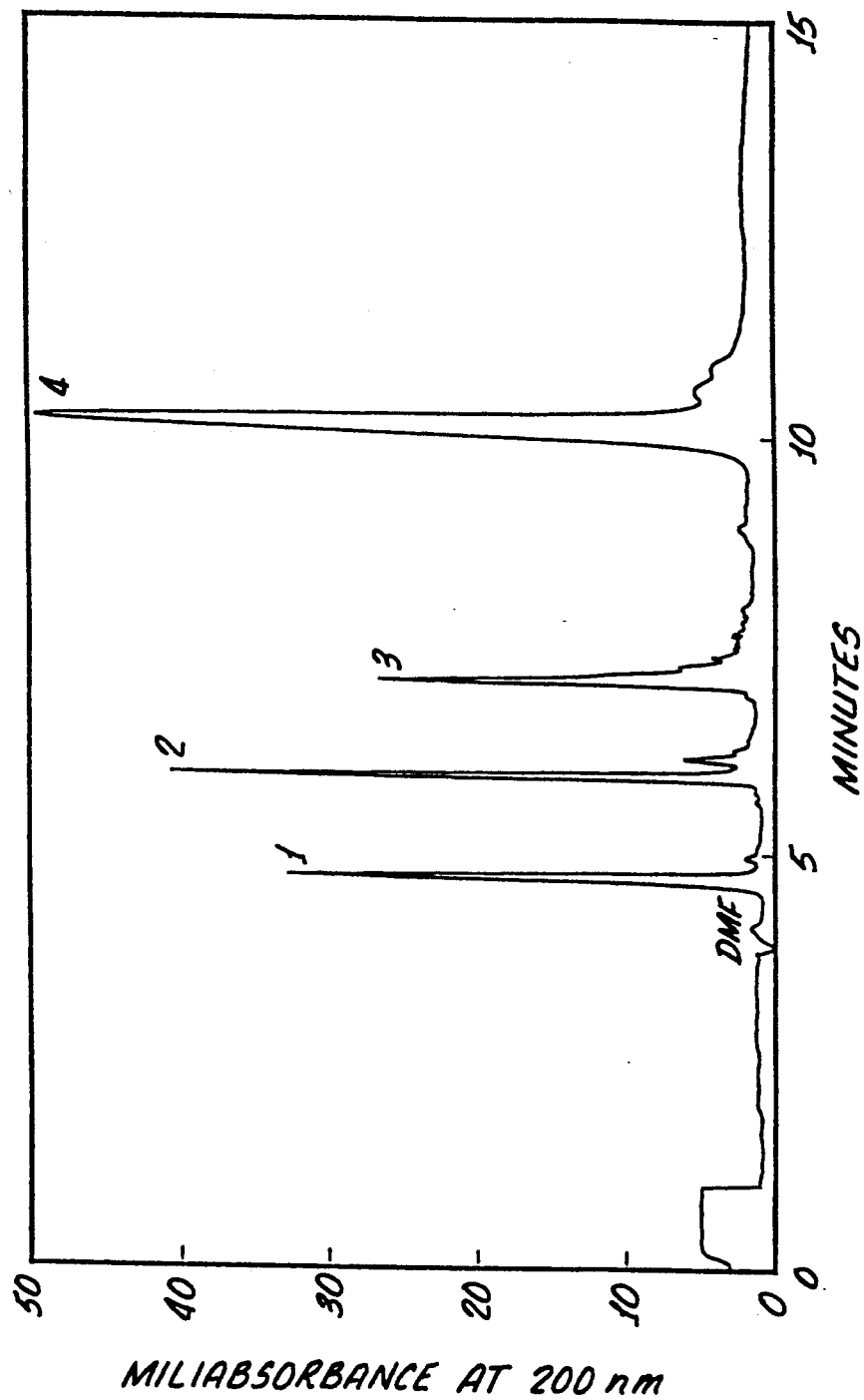
FIG. 5 is an electropherogram of the four model proteins and marker of FIG. 1 in dynamic coating buffer, pH 10.0.

Upon ionization, the interior wall of an untreated fused-silica capillary will have exposed poly-silanol groups. This can be represented schematically as follows (including a schematic representation of a protein constituent):

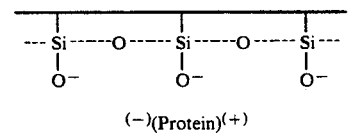

$$(-)(\text{Protein})(+)$$

Accordingly, when the pH of the buffer leads to a protein constituent having a net positive charge, these constituents can become bound to the silanol groups, with concomitant deleterious effects.

Applicant avoids these problems by utilizing a dynamic coating buffer as the electrolytic buffer. A dynamic coating buffer is a pH buffer solution comprising at least one agent capable of chemically reacting with an untreated fused silica material and physically interacting by solvation with at least one ionized sample constituent, and having the following characteristics: (a) at least two dissociation constants ("pKa") and (2) high ionic strength, i.e., the molarity of the agent is at least about 0.2M.

Examples of the agent include phosphoric acid, alkali-metal phosphates having at least one proton, mono-, di-, tri-, and tetra-alkyl ammonium phosphate having from about 1 to about 8 carbon atoms, alkyl phosphate having from about 1 to about 20 carbon atoms, carbonic acid, alkali-metal carbonates having at least one proton, mono-, di-, tri-, and tetra-alkyl ammonium carbonate having from about 1 to about 8 carbon atoms, and alkyl carbonate having from about 1 to about 20 carbon atoms.

Phosphoric acid is illustrative of the operation of the agent; however, the invention is not limited to phosphoric acid as the agent. Phosphoric acid has three defined dissociation constants, i.e., at three specific and different pH values, phosphoric acid will lose a proton:

| Phosphoric Acid form | pKa |
| --- | --- |
| $H_3PO_4$ | No proton loss at pH less than about 2.1 |
| $H_2PO_4^-$ | 2.1 |
| $HPO_4^=$ | 6.8 |
| $PO_4^\equiv$ | 10.8 |

Beneficially, at pH below about 1.9, untreated fused silica does not have a charged surface. As such, adsorption of charged sample constituents is not a consideration. At pH of greater than about 2.1, phosphoric acid from the buffer is capable of interacting with both the silanol groups and the positively charged sample constituents, schematically represented as follows:

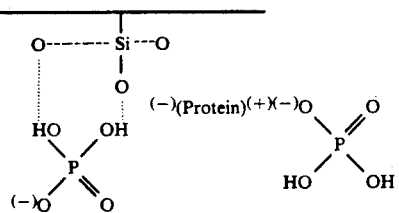

Accordingly, the agent acts to both "coat" the capillary and to "protect" ionized protein constituents. Because of this, the tendency of the positively-charged "patch" of the protein to be adsorbed onto the capillary wall is greatly diminished, because the agent provides an overall negative charge barrier between the silanol groups and the sample constituents and because the agent insures that the sample constituent will evidence an overall net negative charge.

Preferably, the molarity range of the agent is between about 0.2M and about 1.0M, more preferably between about 0.4M and about 0.6M and most preferably about 0.5M. As the molarity ("M") of the agent increases or decreases, the temperature at which the analysis is conducted may also increase or decrease, respectively. Preferably the temperature range for analysis is between about 4° C. and about 60° C. Typically, the CZE analysis is conducted at room temperature.

The buffer of the present invention may contain any other material that does not interfere with the functional behavior of the agent. Examples of materials which may be in the buffer include acetic acid, 2-(N-morpholino) ethanesulfonic acid, 3-(N-morpholino) proponesulfonic acid, N-[tris-hydroxymethyl) ethyl] glycine, tris-(hydroxymethyl) aminomethane, cyclohexyl aminoethane - sulfonic acid, triethyl amine, dimethyl amine, the alkyl amides having up to about 12 carbon atoms, N-2-hydroxyethy 1 piperazine-N'-3-propane sulfonic acid, piperazine-N, N'-bis (2-ethanesulfonic acid), 3-{[tris-(hydroxymethyl) methyl] amino} propanesulfonic acid, 2-{[(hydroxymethyl)methyl] amino} ethanesulfonic acid, and urea.

Preferably, the agent or a combination of agents, are the sole constituents of the dynamic coating buffer. In a particularly preferred embodiment of the invention, mono-, di-, and tri-sodium phosphate are utilized. Mono-sodium phosphate ($NaH_2PO_4$) has a pH of about 4.0; di-sodium phosphate ($Na_2HPO_4$), has a pH of about 9.0; tri-sodium phosphate ($Na_3PO_4$) has a pH of about 11.0. Most preferably, the molarity of each of these is 0.5M, although different molarities for each can be utilized. When the molarities are the same, however, the manipulation of pH is more efficiently accomplished. I.e., if the desired pH of the buffer is between about 4.0 and about 9.0, then aliquots of $NaH_2PO_4$ and $Na_2HPO_4$ can be admixed until the desired pH is achieved; if the desired pH of the buffer is between about 9.0 and about 11.0, then aliquots of $Na_2HPO_4$ and $Na_3PO_4$ can be admixed until the desired pH is achieved.

The foregoing methodology of achieving a desired pH value can be utilized with a pH buffer other than the agent. This would entail selecting a pH buffer having a known pKa and admixing it with an agent having a known pKa until the desired pH is achieved. Similarly, dynamic pH buffer kits comprising a series of dynamic pH buffers each having a different pH value would be beneficial; such a kit would allow any investigator to select a dynamic coating buffer from the kit that has the pH value of interest.

EXAMPLES

The following examples directed to preferred embodiments of the invention disclosed herein are at intended, nor should they be construed, as limiting to disclosure, or the claims to follow:

I. MATERIALS AND METHODS

A. Capillary Electrophoresis Procedures

Capillary electrophoresis of samples was performed on Beckman Instruments, Inc. high performance capillary electrophoresis system (Beckman Instruments, Inc., Fullerton CA., USA, Model No. 357575). Data analysis was performed on System Gold ™ software (Beckman Instruments, Inc.). The aforementioned capillary electrophoresis system contains built-in 200, 206, 214, 280 and 340 nm narrow-band filters for on-line detection and quantification. Electrophoresis was performed in fused silica tubes having 20 μm i.d. and 27 cm long (Beckman Instruments, Inc., part no. 338475) or 20 μm and 25 μm i.d., 25 cm long (Polymicro Technologies, Inc., Phoenix, AZ., USA, part nos. TSP020374 and TSP025375). The detection window is located approximately 6.5 cm from the column outlet.

Samples were placed on the inlet tray of the above-described capillary electrophoresis system, and introduced into the capillary by pressure injection for about 20 to about 40 seconds. Except as otherwise indicated in the following Examples, the capillary was sequentially washed between runs with two column volumes of 1.0N sodium hydroxide (base) and water (0.3 min high pressure), followed by reconditioning with five to ten column volumes of dynamic coating buffer (1.5 to 2.5 min high pressure). Sample constituents were separated using a column voltage gradient of between 210 volts/cm and 450 volts/cm.

B. DYNAMIC COATING BUFFER

Mono-sodium phosphate (pH 4.0, 0.5M), di-sodium phosphate (pH 9.0, 0.5M) and tri-sodium phosphate (pH 11.0, 0.5M) were from Sigma Biochemicals. The buffers were prepared from each of the salts to obtain dynamic coating buffers having pH values of 5.0, 6.0, 7.0, 8.0, 9.0 and 10.

C. MODEL PROTEINS

Model Protein Set A consisted of Bovine lung trypsin inhibitor (pI=10.5, MW=500) (electropherogram peak thereof is referenced in the Figures as "1"), Cytochrome c (pI - 10.65, MW=12,500) ("2"), Carbonic anhydrase (pI=5.9, MW=29,000) ("3"), and soybean trypsin inhibitor (pI - 4.5, MW=21,000) ("4"). Model Protein Set A was obtained from Serva Biochemicals (Westbury, N.Y., USA, Product No. 39209). Model Proteins for Set B were obtained from Sigma Biochemicals (St. Louis, MO. USA) and consisted of Horse heart myoglobin (pI 7.0, M.W.=17,500; Sigma Product No. M 1882) ("5"), Conalbumin (pI=6.6, M.W.=77,000; Sigma Product No. C 0755) ("6"), Beta.lactoglobulin B (pI=5.4, M.W.=35,000; Sigma Product No. L 8005) ("7"), and Beta-lactoglobulin A (pI=5.2, M.W.=35,000; Sigma Product No. L 7880) ("8").

Model proteins were dissolved in diluent buffer (PBS) containing 75mM sodium chloride, 20mM potassium phosphate, 0.01% sodium azide, pH 7.0. Each model protein concentration was 0.3 to 1.0 mg/ml. A 0.01% v/v of dimethyformamide ("DMF") was added to the diluent buffer as an EOF marker. All chemicals were at least of ACS grade.

D. SERUM SAMPLES

Normal control sample of serum protein was obtained from Beckman Instruments, Inc., Fullerton, CA. Serum sample was diluted in the aforementioned diluent buffer in a 1 to 20 ratio (serum sample to diluent). DMF was added to the diluted sample as described above.

E. MILK SAMPLES

The major protein components of cow's milk, β-casein, α-lactalbumin, β-lactoglobulin B, α-casein, and β-lactoglobulin A were separated for four (4) milk conditions: non.fat; low-fat (2%); whole; and powdered. Milk samples were obtained from grocery stores and refrigerated. Powdered milk was prepared with tap water. Milk samples were diluted in a ratio of 1 part sample to 5 parts Beckman ICS TM Diluent (Beckman Instruments, Inc.). The dynamic coating buffer was as described above, except that urea (final concentration: 4M) was added to the buffer in order to prevent aggregation of casein proteins. DMF was added to the diluted samples as described above.

II. EXAMPLES

EXAMPLE I Analysis of Dynamic Coating Buffer Over Wide pH Range: Set A Model Proteins FIGS. 1-5, respectively, are electropherograms of the separations of the Set A Model Proteins with 0.5M sodium phosphate buffer at pH 5.0, 6.0, 7.0, 9.0 and 10.0. Conditions for each run were as follows:

| Figure | Capillary | | v/cm | μA |
| --- | --- | --- | --- | --- |
| | i.d. | length | | |
| 1 | 25 μm | 21 cm | 350 | 34 |
| 2 | 25 μm | 21 cm | 350 | 46 |
| 3 | 25 μm | 21 cm | 350 | 46 |
| 4 | 25 μm | 21 cm | 350 | 79 |
| 5 | 25 μm | 21 cm | 220 | 69 |

Absorbance was at 200 nm for each run. As is evident, excellent resolution was achieved at all pH levels.

Several trends are of interest. At pH 7.0, bovine lung trypsin inhibitor (1, pI=10.5) and cytochrome c (2, pI=10.65), based upon their respective pI values, migrate earlier in time than the DMF neutral marker, as would be expected. Carbonic anhydrase (3, pI=5.9) would be expected to migrate earlier in time than the DMF marker at pH 5.0 and close to that marker at pH 6.0. However, carbonic anhydrase migrates much later than the DMF marker at pH 5.0 and 6.0. At pH 9.0, cytochrome c migrates after the DMF marker; however, it would be predicted that cytochrome c should migrate before the marker at pH 9.0. The same type of anomalous results are evidenced for cytochrome c and bovine lung trypsin inhibitor at pH 10.0.

While not wishing to be bound to any particular theory, Applicant postulates that the anomalous results are explained by solvation of the positively charged moieties of the protein by the buffer counter ions. As used herein, the term "solvation" means that the agent and a sample constituent physically interact such that the two molecules behave as one, without chemically reacting in such a manner that the agent alters or otherwise changes the chemical characteristics of the constituent. Thus, the solvation effect can significantly modify the isoelectric point of the protein. I.e., the agent, by physically interacting with the charged protein, alters the charge density of the protein such that the migration thereof can become altered from an expected or predicted migration relative to a neutral marker.

These results indicate that separation of the Set A proteins can be obtained over a variety of pH values, notably at neutral pH of 7.0, in an untreated capillary column.

Figure 6:
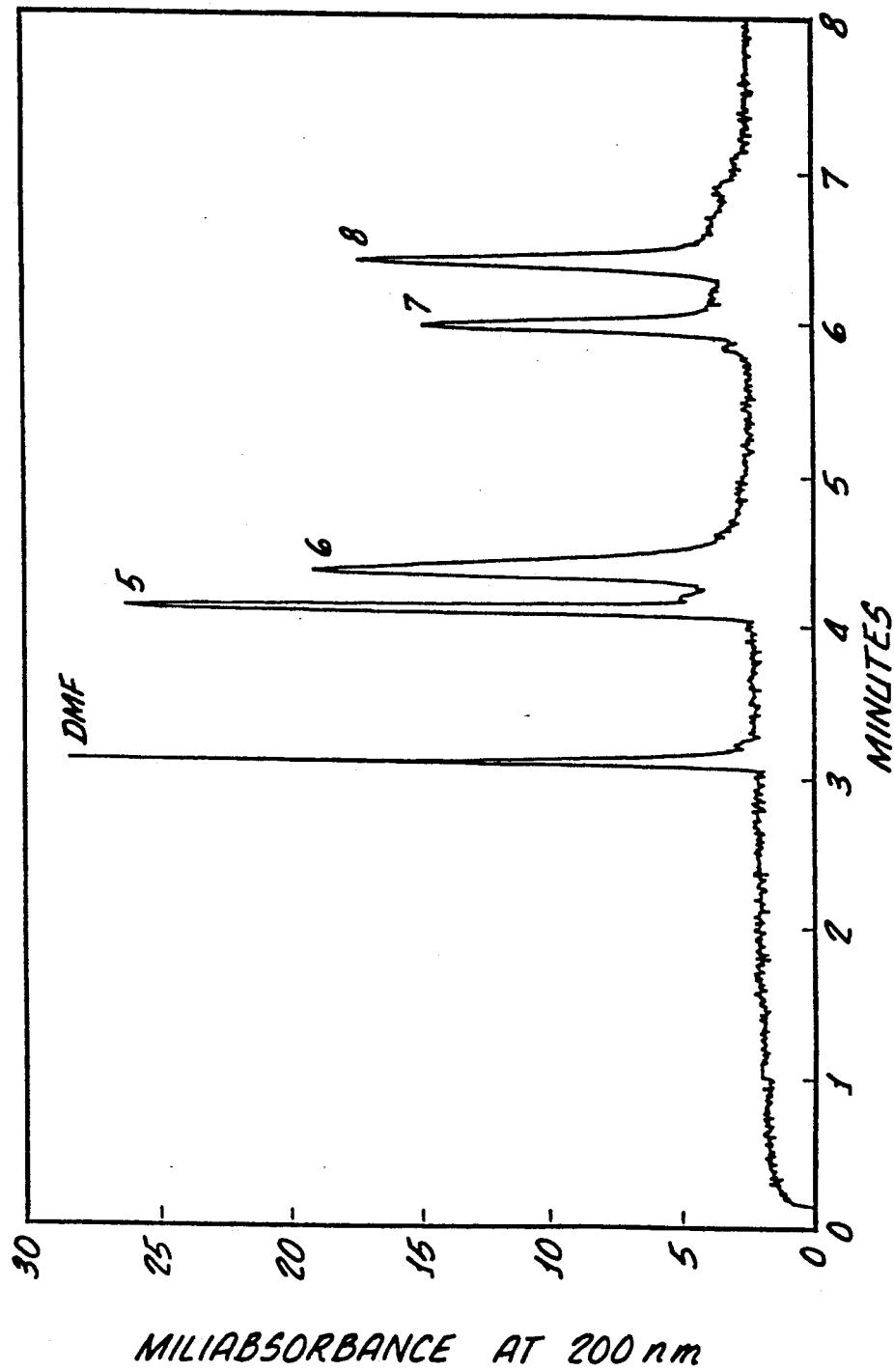
FIG. 6 is an electropherogram of four model proteins and a neutral marker (DMF) in dynamic coating buffer, pH 7.0.
Figure 7:
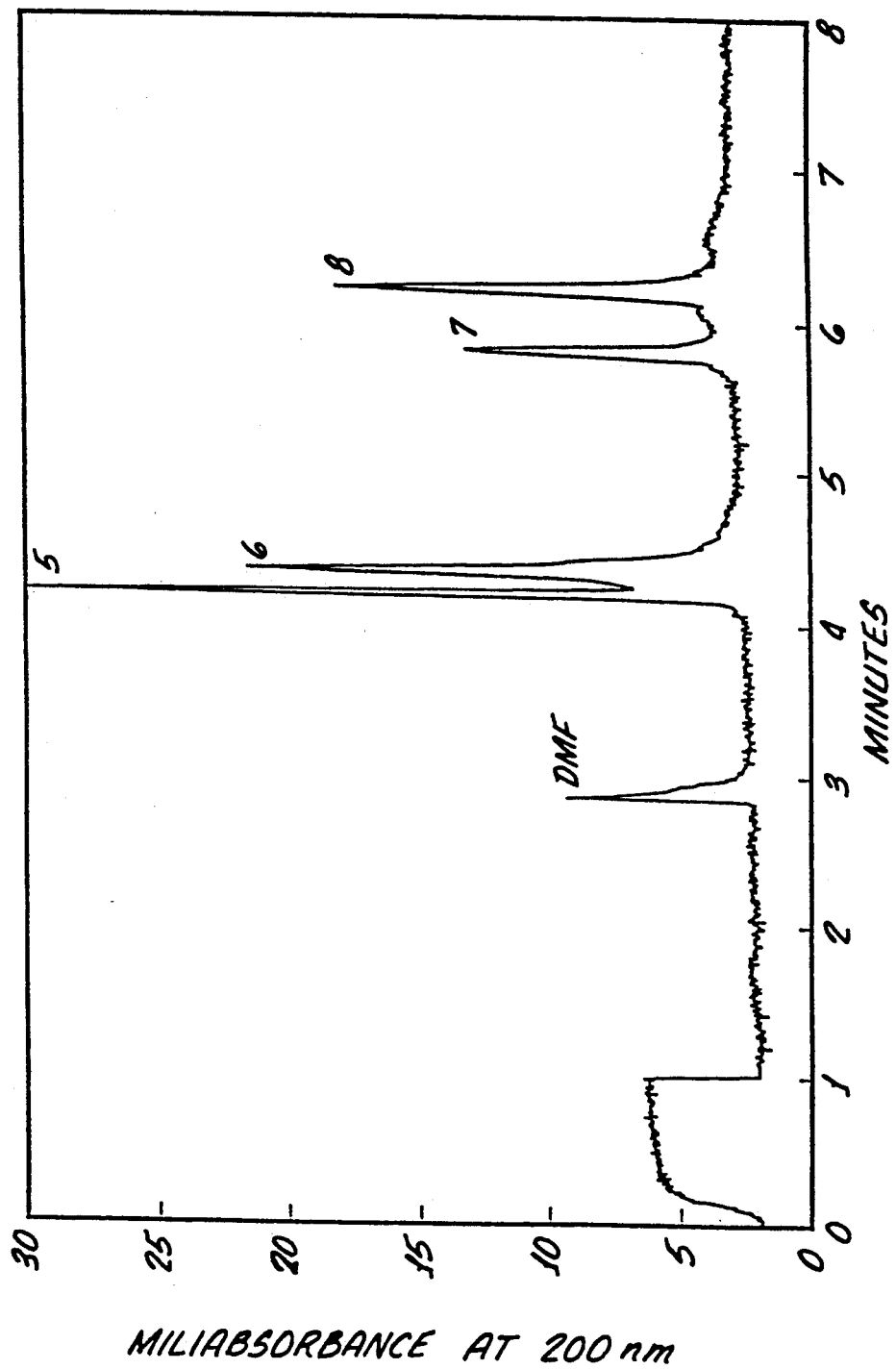
FIG. 7 is an electropherogram of the four model proteins and marker of FIG. 6 in dynamic coating buffer, pH 9.0.

EXAMPLE II Analysis of Dynamic Coating Buffer Over Narrow pI Range: Set B Model Proteins FIGS. 6-7, respectively, are electropherograms of Model Protein Set B with 0.5M sodium phosphate buffer at pH 7.0 and 9.0, respectively. Conditions for each run were as follows:

| Figure | Capillary | | v/cm | μA |
| --- | --- | --- | --- | --- |
| | i.d. | length | | |
| 6 | 20μ | 22 cm | 410 | 73 |
| 7 | 20 μm | 22 cm | 410 | 96 |

Absorbance was at 200 nm for each run. As is evident, efficient separations were achieved at these pH values. Of note is the well-resolved separation of beta-lactoglobulin B and A (peak 7 and 8, pI=5.3 and 5.1, respectively). These results demonstrate that protein species with a pI difference of 0.2 can be separated using the dynamic coating buffer disclosed herein.

Figure 8:
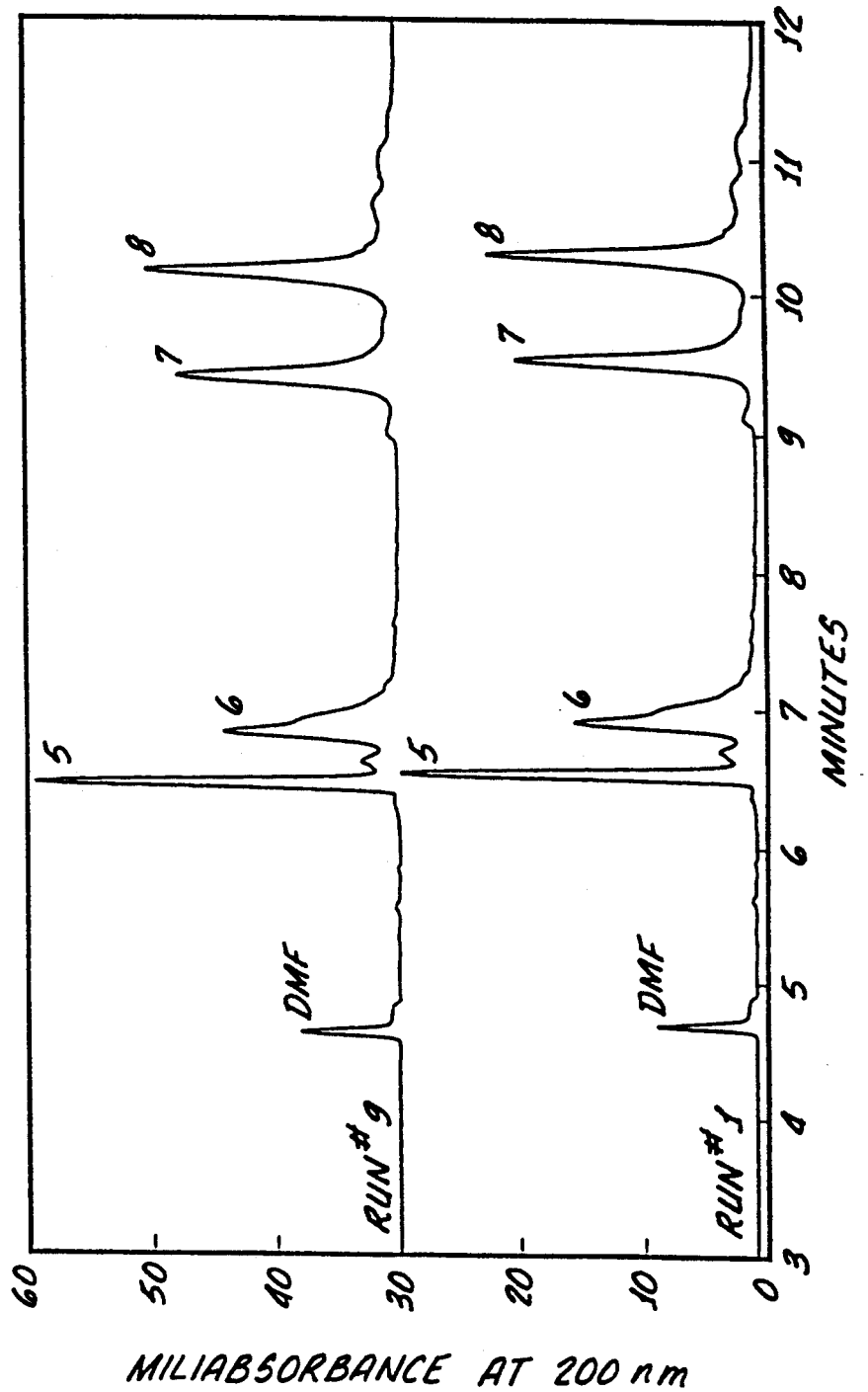
FIG. 8 is a reproducibility overlay of two electropherograms of the four model proteins and marker of FIG. 6 in dynamic coating buffer, pH 7.0, one at run 1, and the other at run 9.

Nine consecutive runs of Set B Model Proteins (with washing and reconditioning between each run, as described), were conducted at pH 8.0 (25 μm×21 cm capillary; 350 v/cm; 90 μA; 200 nm absorbance). FIG. 8 provides the electropherograms of the first and ninth runs, which are nearly identical. These results indicate the precision in migration times associated with the dynamic coating buffer disclosed herein.

EXAMPLE III Analysis of Serum Protein

Previous attempts at analyzing human serum proteins in untreated fused-silica capillary columns required the use of buffer having pH of greater than about 9.0. See, Chen, F-T A. et al, "Capillary Electrophoresis - A New Clinical Tool." Clin. Chem. 77/1: 14–19(1991), which is incorporated herein by reference.

Figure 9:
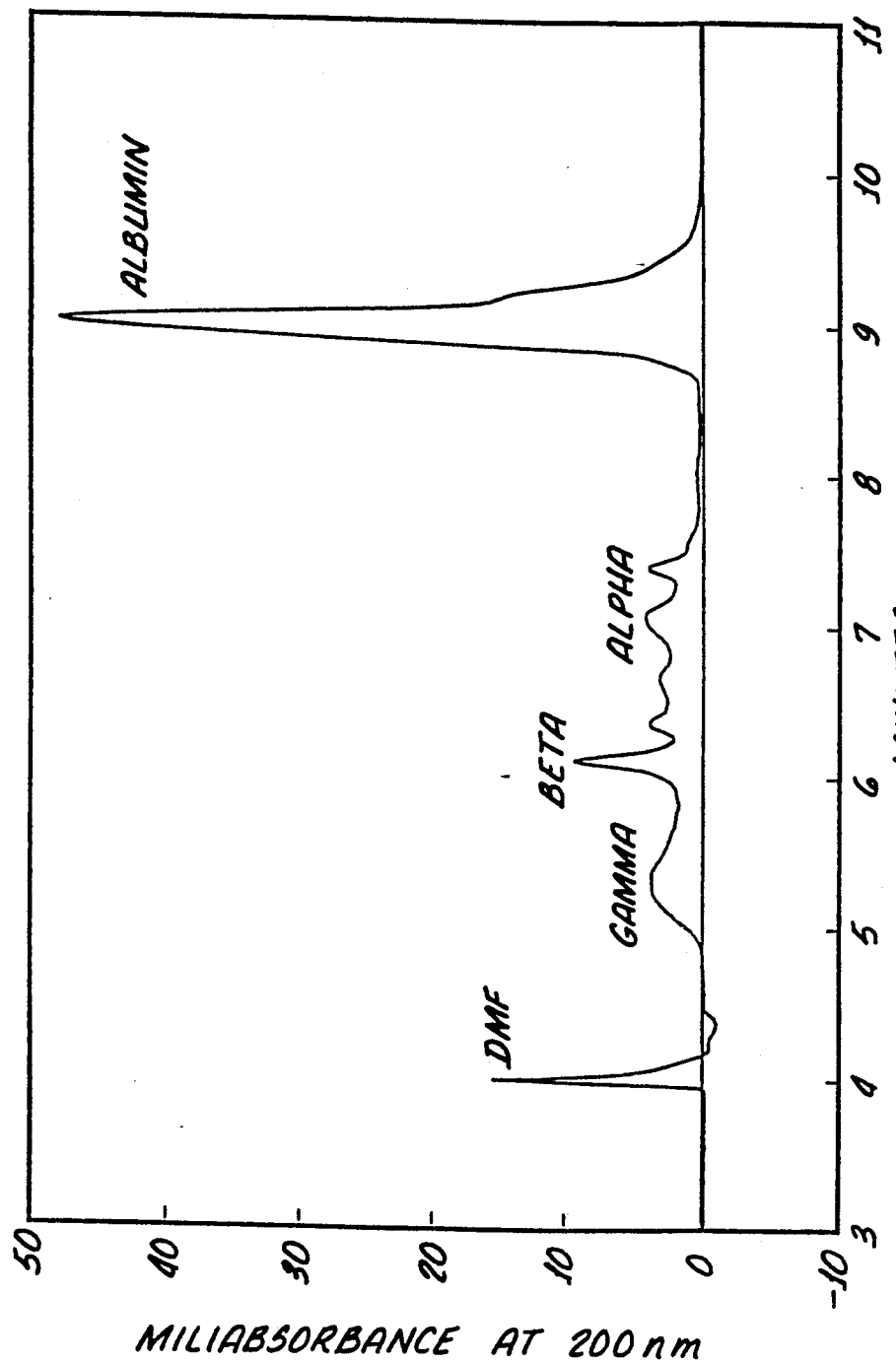
FIG. 9 is an electropherogram of serum proteins and a neutral marker (DMF) in dynamic coating buffer, pH 7.0.
Figure 10:
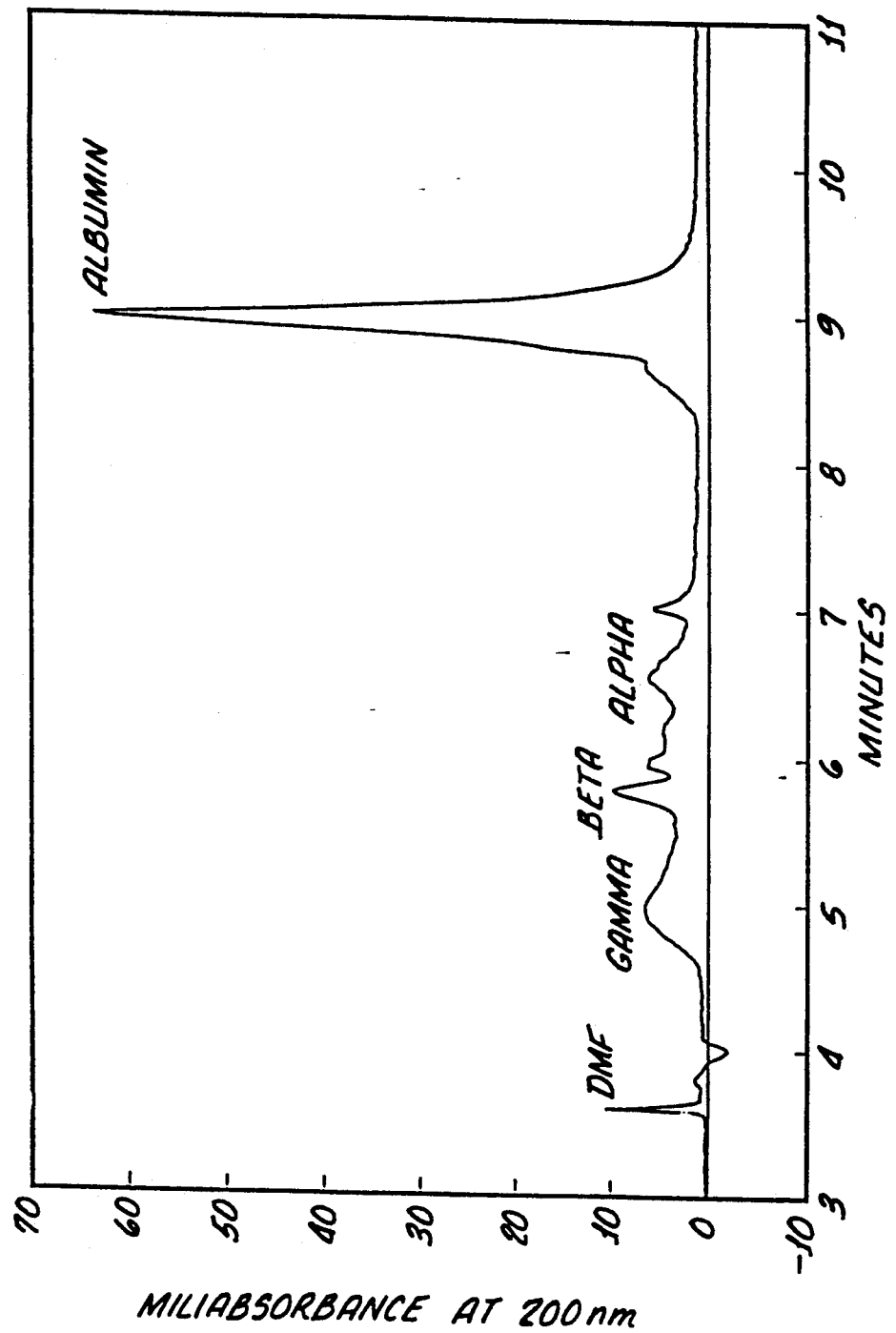
FIG. 10 is an electropherogram of serum proteins and internal marker in dynamic coating buffer, pH 8.0.

FIGS. 9-10 are electropherograms of the separation of serum proteins using 0.5M sodium phosphate, pH 7.0 and 8.0, respectively. As is evident, a well-defined separation of serum proteins is achieved at both pH 7.0 and 8.0 using the dynamic coating buffer disclosed herein.

EXAMPLE IV

Analysis of Milk Proteins

Figure 11:
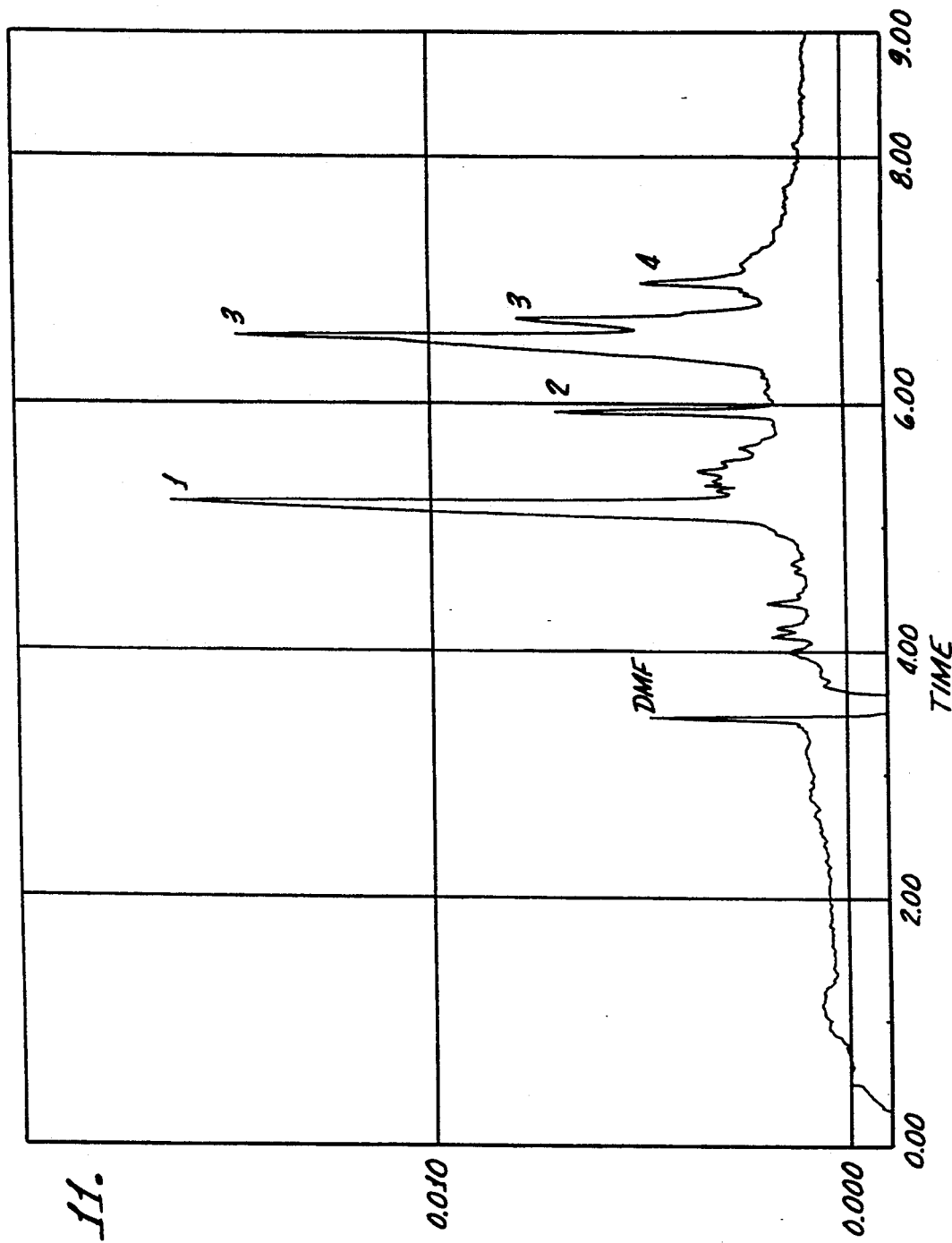
FIG. 11 is an electopherogram of protein separations of non-fat milk.
Figure 12:
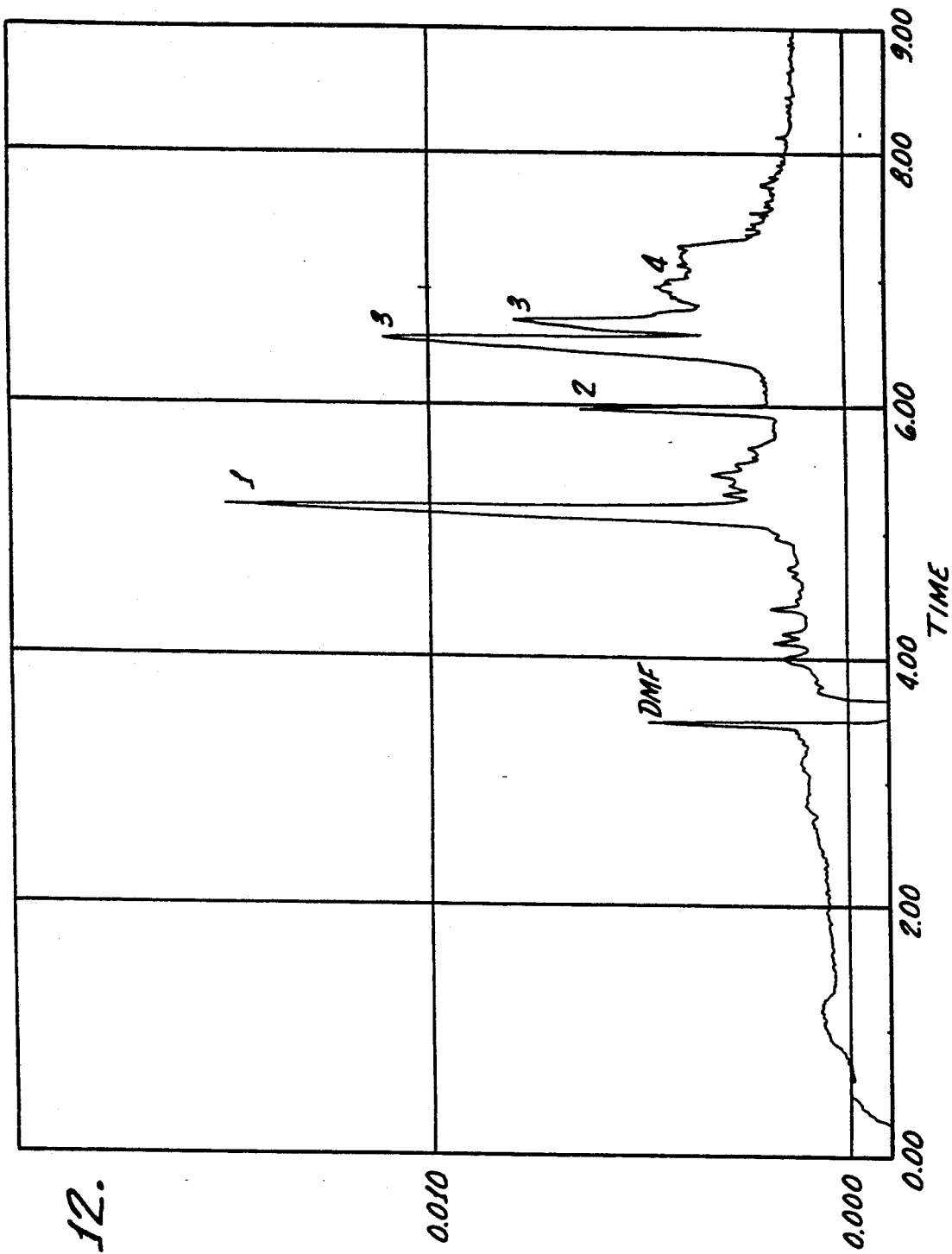
FIG. 12 is an electopherogram of protein separations of low-fat (2%) milk.
Figure 13:
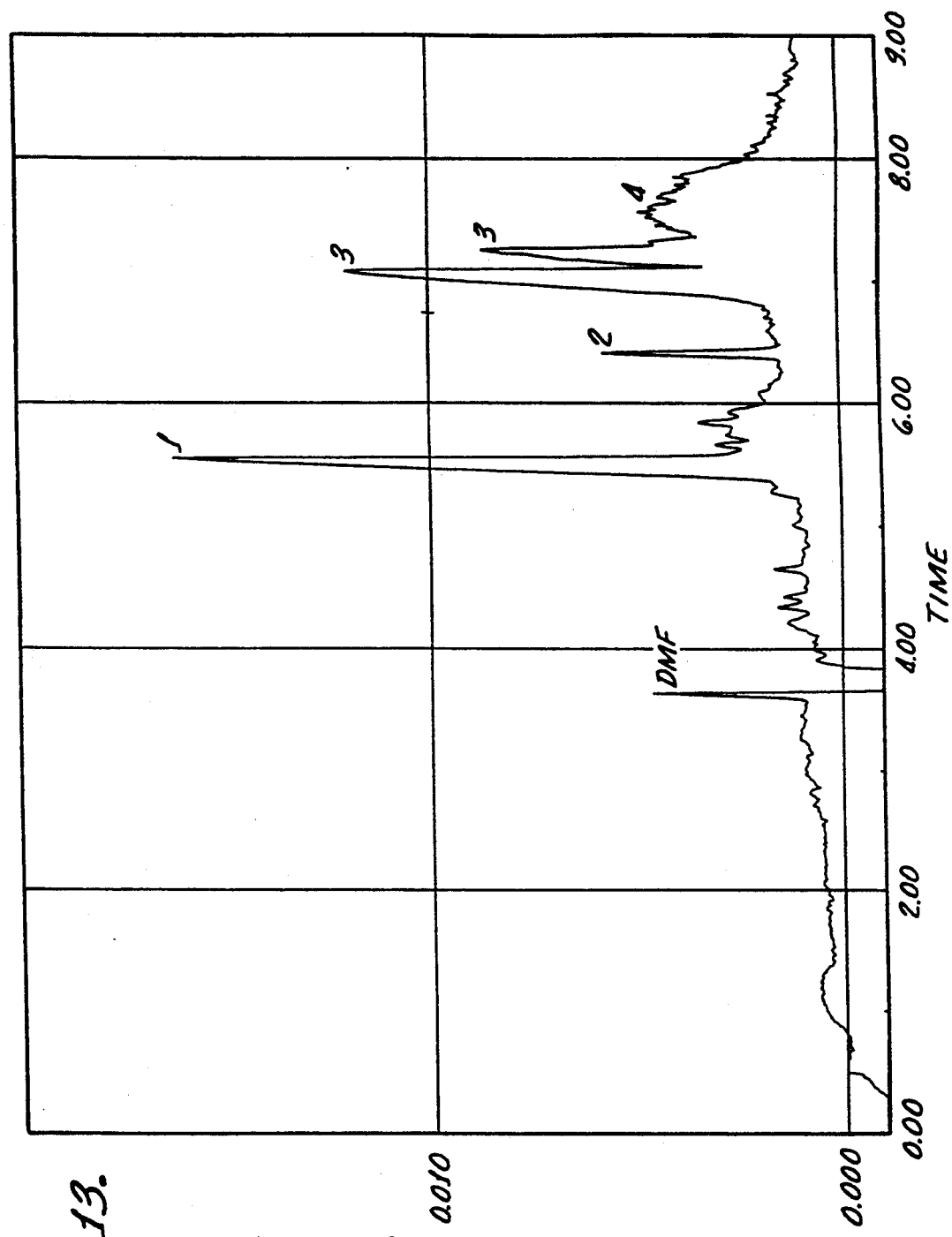
FIG. 13 is an electopherogram of protein separations of whole milk.
Figure 14:
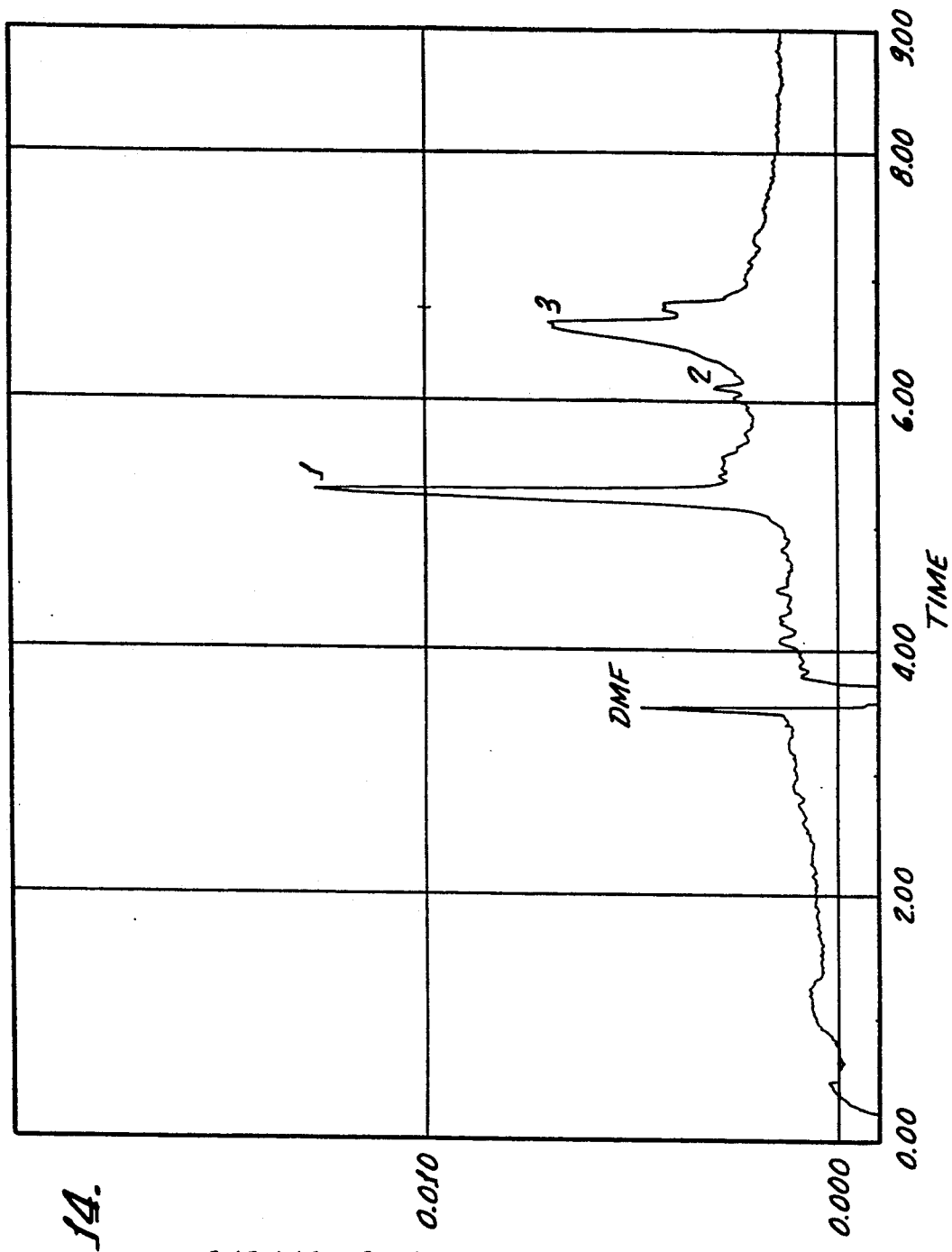
FIG. 14 is an electopherogram of protein separations of powdered milk.

The major proteins of various forms of milk were analyzed. Well-defined separations of the protein components of non-fat milk (FIG. 11), low-fat (7) milk (FIG. 12), whole milk (FIG. 13), and powdered milk (FIG. 14) are evident. Peaks are as follows: $\beta$-casein-1; $\alpha$-lactalbumin-2; $\beta$-lactoglobulin B and $\alpha$-casein-3; and $\beta$-lactoglobulin A-4.

An interesting trend was evidenced by the analyses presented in the electropherograms of FIGS. 11-14. Note that for the non-powdered milk forms, the $\alpha$-lactalbumin peak (2) is unique, but for powdered milk, this peak is quite minor. For all types of milk, the peak for $\beta$-casein (1) is a major peak. This facet allows for an interesting manner to determine if a milk sample has been adulterated with powdered milk. The addition of powdered milk to non-powdered milk could be detected by, e.g., dividing the area of the absorbance peak of $\alpha$-lactalbumin into that of $\beta$-casein.

To test the theory, various percentages of rehydrated powdered milk were added to non-fat milk and the resulting absorbance areas for $\alpha$-lactalbumin and $\beta$-casein (which can be automatically derived by the aforementioned System Gold ™ Software) were obtained. Results are set forth below in Table 1):

TABLE 1

| Component Percentage Powdered: Non-Fat | Area Ratio* |
|---|---|
| 75%:25% | 12.3 |
| 50%:50% | 10.2 |
| 25%:75% | 7.7 |
| 0:100% | 5.7 |

*= $\beta$-casein:$\alpha$-lactalbumin
Buffer = 0.5M sodium phosphate, 4M urea, pH 7.0
Conditions: 10 KV/51 µA These results indicate that as the percentage of powdered-milk adulteration increases, the ratio of peak area for $\beta$-casein to $\alpha$-lactalbumin increases.

EXAMPLE V

Dynamic Coating Validation

In a typical CZE analytical evaluation, a wash step takes place between each sample run. Regardless of whether or not the column is coated, there is an inevitable adsorption of sample constituents to the capillary wall. The wash step ensures, inter alia, that such adsorbed constituents are removed from the wall. In an untreated capillary, the adsorption of sample constituents would be much greater.

Adsorption of sample constituents has at least one serious affect from a run-to-run perspective: it significantly extends the time necessary to conduct the CZE analysis between runs. That is because as the material becomes adsorbed to the column, the charge density of the surface decreases, and then has to effect of, inter alia, decreasing electroendosmetic flow.

A dynamic coating buffer should result in faster analysis between runs until a "coating" equilibrium is reached. By "faster analysis" is meant that later runs of a sample should reach the detection window before earlier runs of the same sample. By "coating equilibrium" is meant that as the agent "coats" the column, a point will be reached where substantially all of the column is "coated" such that after this point, an analytical run of a sample should reach the detection window at about the same time as later analytical runs of that sample. The explanation for this increase in speed is based upon the interaction between the agent and silanol groups; because both of these groups are negatively charged upon ionization of the capillary, and because the agent is also capable of interacting with the silanol groups via hydrogen bonding; the charge density of the dynamically coated constituents increases, thus leading to the increased electroendosmotic flow.

In conjunction with such coating would be interaction between the agent and the sample constituents. I.e., solvation of the sample constituents by the agent would be expected to occur. Because the sample constituents are solvated by the agent, the overall charge of the solvated constituent would be the same as the overall charge of the capillary inner wall; this relationship would substantially diminish adsorption of the constituents to the capillary inner wall.

Figure 15:
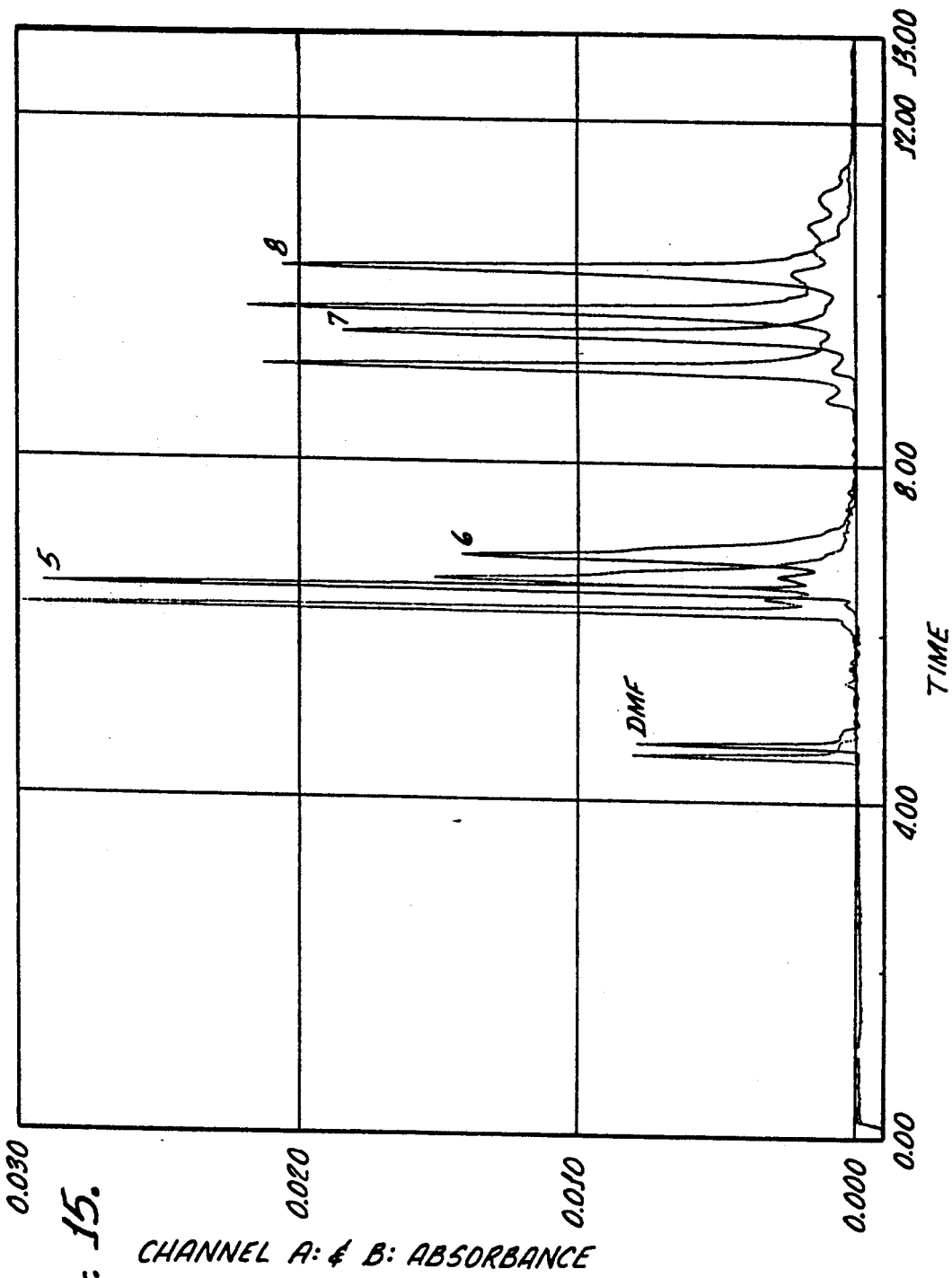
FIG. 15 is an electropherogram of a first run (bold line) and third run (dashed line) of Set B Model Proteins without wash and reconditioning steps between each run.
Figure 16:
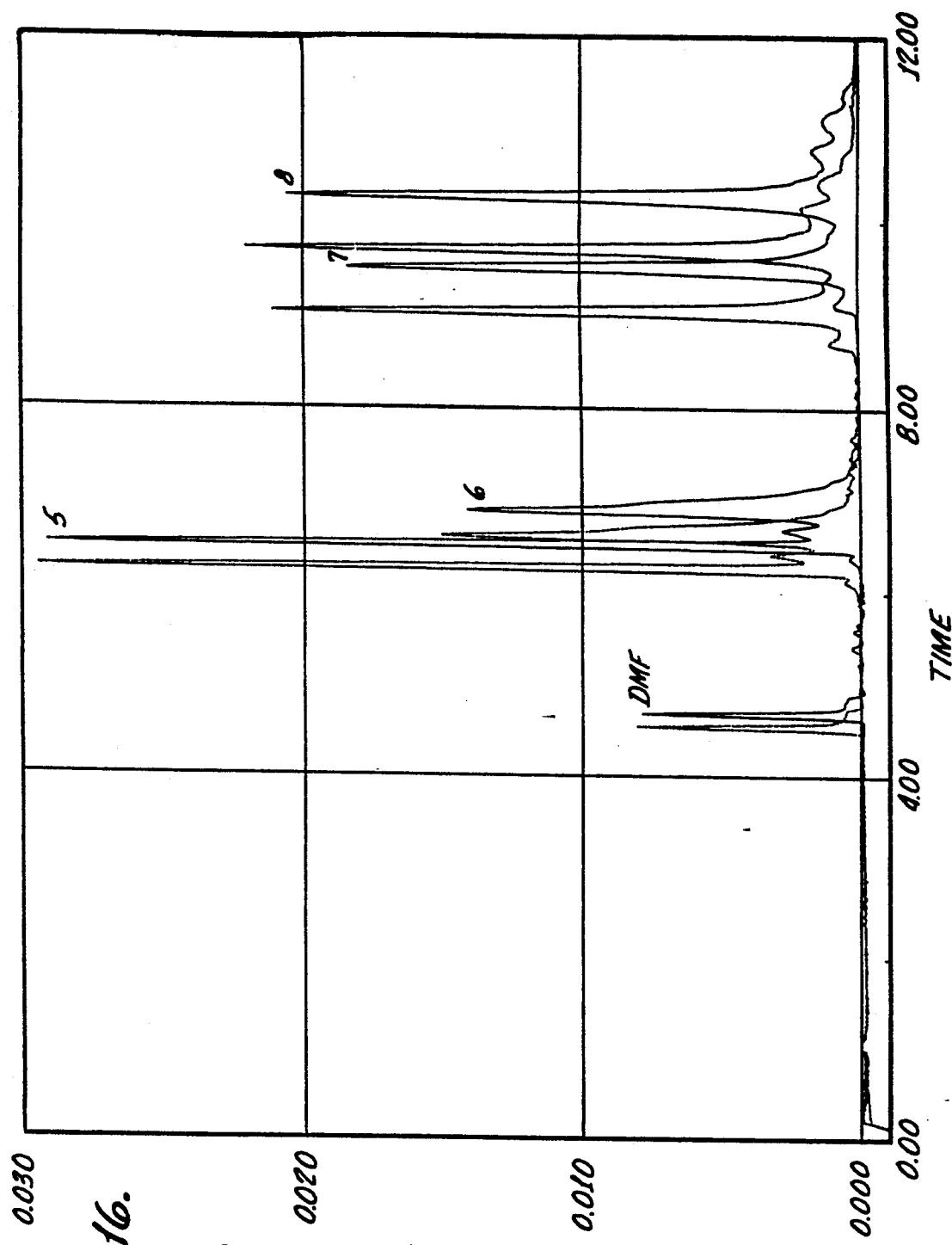
FIG. 16 is an electropherogram of a first run (bold line) and fifth run (dashed line) of Set B Model Proteins without wash and reconditioning steps between each run.
Figure 17:
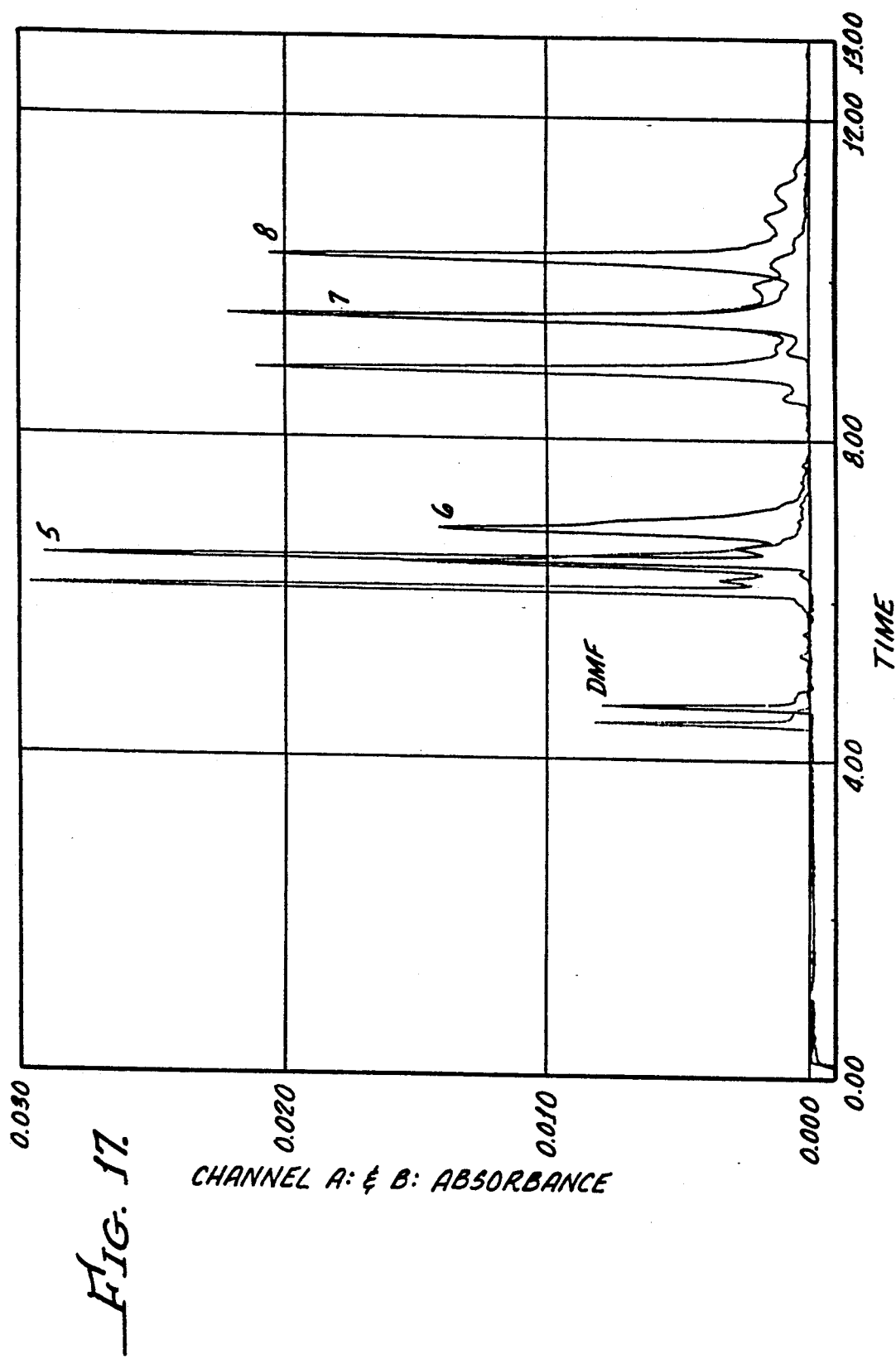
FIG. 17 is an electropherogram of a first run (bold line) and seventh run (dashed line) of Set B Model Proteins without wash and reconditioning steps between each run.
Figure 18:
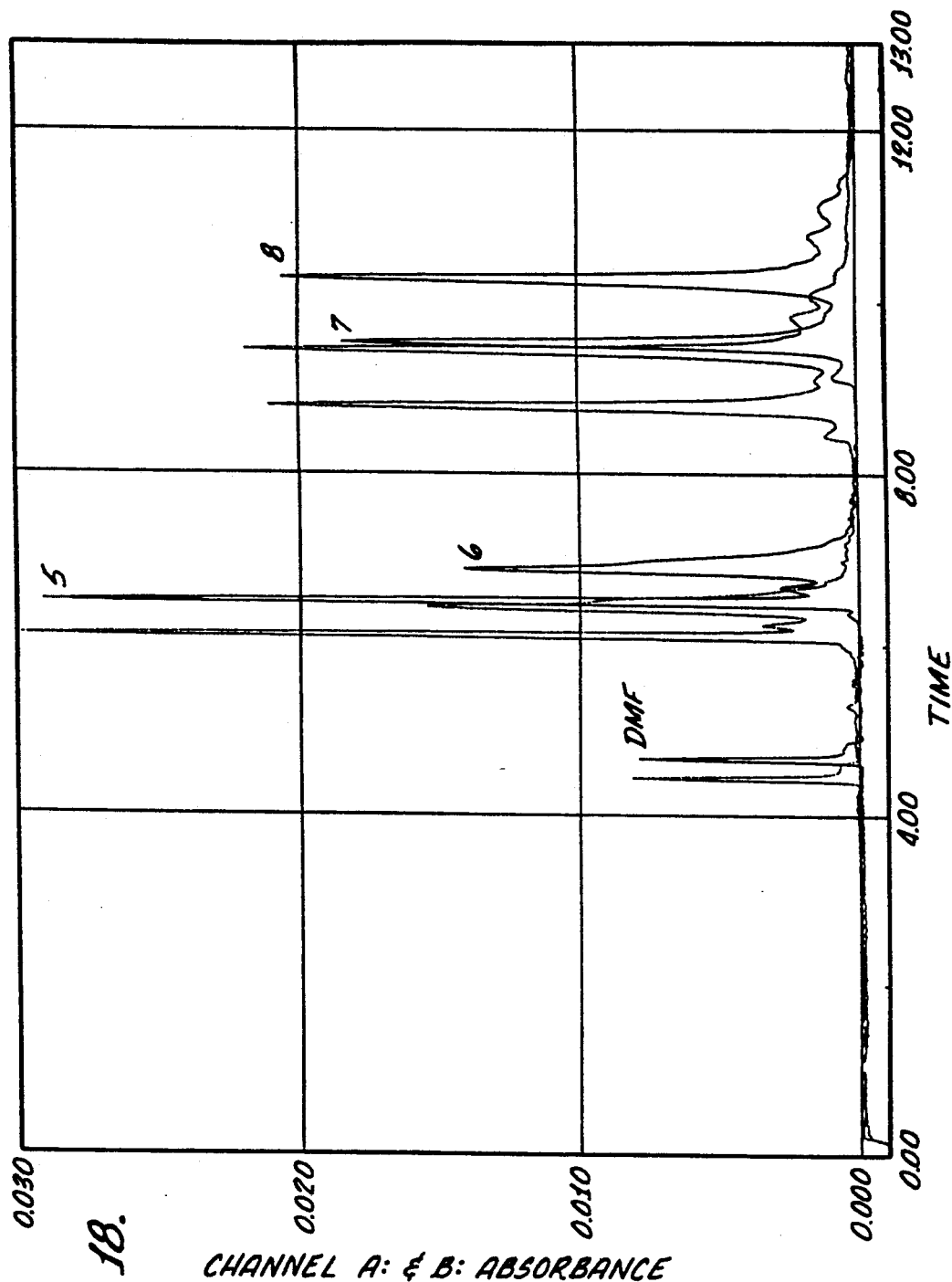
FIG. 18 is an electropherogram of a first run (bold line) and ninth run (dashed line) of Set B Model Proteins without wash and reconditioning steps between each run.
Figure 19:
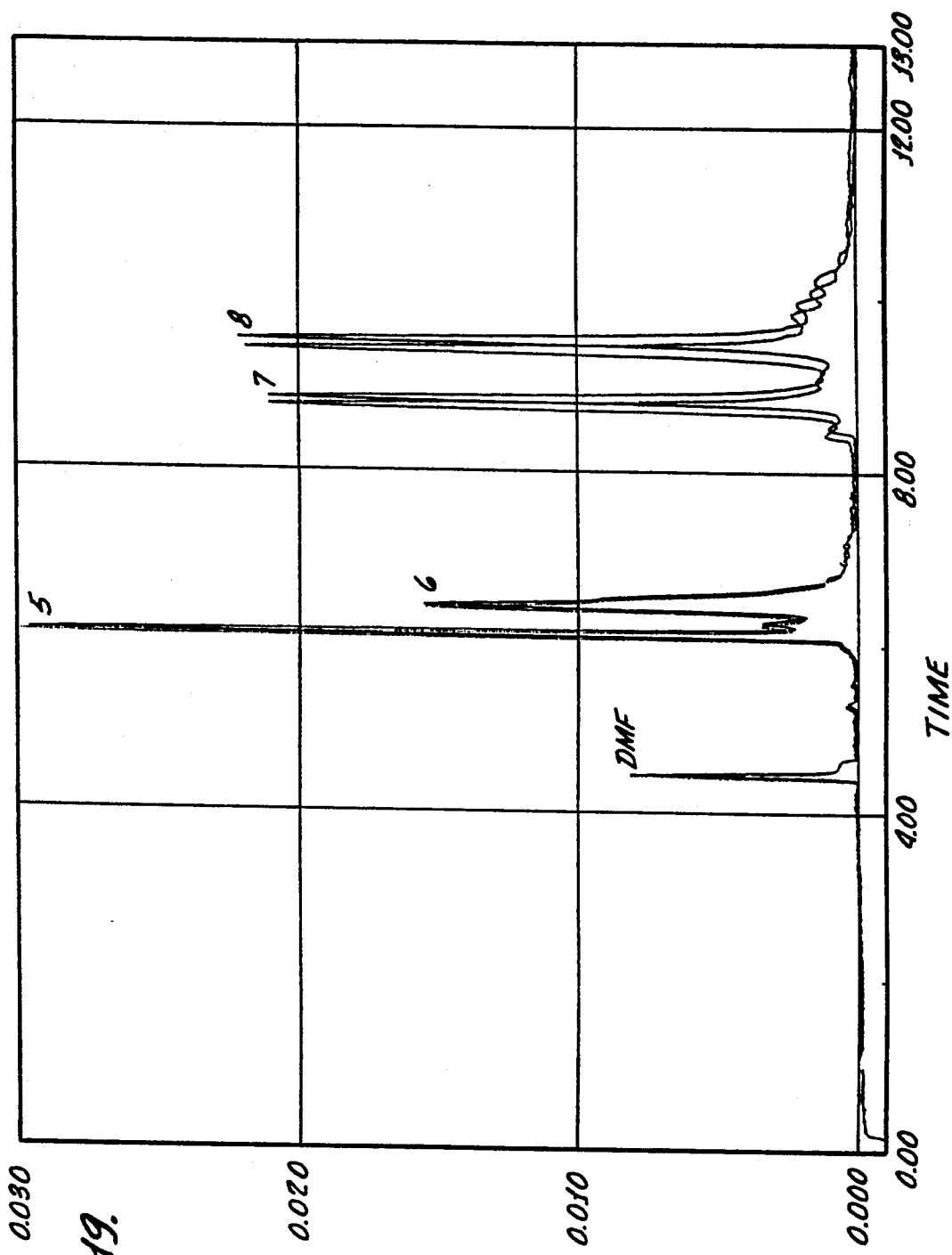
FIG. 19 is an electropherogram of a seventh run (bold line) and ninth run (dashed line) of Set B Model Proteins without wash and reconditioning steps between each run.

To validate the concept of a dynamic coating buffer, several CZE analytical runs were conducted on the Model Protein Set B without the wash and reconditioning steps between runs. Between sample runs, the capillary was filled with the dynamic coating buffer, pH 7.0. FIG. 15 provides electropherograms of the first and third runs of Set B, with the first run in bold line and the third run in dashed line. The electropherograms indicate that the third run precedes (in comparative time) the first run. FIG. 16 provides a similar electropherogram comparison between the first run (bold) and the fifth run (dashed) of Set B. Again, the fifth run precedes (in comparative time) the first run. Similar results are evidenced in FIG. 17 (first run-bold, seventh run-dashed) and FIG. 18 (first run-bold, ninth run-dashed). FIG. 19 provides a comparison between the seventh and ninth runs (seventh run-bold, ninth run-dashed) of Set B. These electrophaograms are nearly identical when superimposed upon one another, i.e. the seventh and ninth runs are nearly the same in comparative analytical time.

These results validate the concept of a dynamic coating buffer. As each run proceeded, those later in time evidenced faster analytical results. Additionally, the nearly identical peak heights and distributions indicate that adsorption of the sample constituents was negligible over time.

EXAMPLE VI

Comparative Analysis: Green

In Green, a 0.1M CHES (2-(cyclohexylamino) ethanesulfonic acid) buffer with 0.25M $K_2SO_4$, pH 9.0, evidenced separation of model proteins. However, serum protein separation using buffer pH conditions of 8.0 or below (zwitterionic buffers) with 0.3M and 0.5M $K_2SO_4$, was not viable. The following conditions set forth in Table 2 were tested and the resulting Figure numbers are for the resulting electropherograms:

TABLE 2

| Buffer | Molarity | pKa | $K_2SO_4$(M) | pH | Figure |
|---|---|---|---|---|---|
| BES | 0.1 | 7.17 | .3 | 7.0 | 20 |
| HEPES | 0.1 | 7.55 | .3 | 7.5 | 21 |
| TAPS | 0.1 | 8.0 | .3 | 8.0 | 22 |
| BES | 0.1 | 7.17 | .5 | 7.0 | 23 |
| HEPES | 0.1 | 7.55 | .5 | 7.5 | 24 |

TABLE 2-continued

| Buffer | Molarity | pKa | K$_2$SO$_4$(M) | pH | Figure |
|---|---|---|---|---|---|
| TAPS | 0.1 | 8.0 | .5 | 8.0 | 25 |

BES - N,N-bis (2-hydroxyethyl-2-aminoethane sulfonic acid
HEPES - 4-(2-hydroxyethyl)piperaxzine-1-ethanesulfonic acid
TAPS - N-[tris(hydroxymethyl)methyl]-3-aminopropane sulfonic acid
Conditions: 25 μm × 23 cm capillary; 350 v/cm; 72-80 μa; 200 nm absorbance As evidenced by the electropherograms of FIGS. 20-27, inclusive, the use of various zwitterionic salts with either 0.3M or 0.5M potassium sulfate did not allow for separation of the serum proteins at pH 8.0 or below.

EXAMPLE VII

Comparative Analysis: Green And Swedberg

As those in the art appreciate, viability of both untreated and treated columns is typically accomplished using purified, model proteins having well-defined characteristics. Model Protein Sets A and B are exemplary. While at a first level this is acceptable, in that the variability associated with other "non-model" proteins is eliminated, at a second level this may be unacceptable—this is because the utility of any column should be evaluated relative to such "non-model" proteins, such as, for example, serum proteins.

The Green protocol described previously was followed with respect to the analysis of Set A proteins using 0.1M HEPES buffer, 0.25M K$_2$SO$_4$, pH 7.0 (HEPES buffer was used instead of CHES because as those in the art appreciate, CHES has no buffer capacity at pH 7.0). The resulting electropherogram of FIG. 26 indicates separation of such proteins was accomplished. In comparison herewith, FIG. 27 provides an electropherogram of the attempted separation of serum proteins using the conditions of FIG. 26. The electropherogram of FIG. 27 indicates the serum proteins were not separated.

With respect to treated, coated columns, the coating described in Swedberg (terminal aryl pentafluoro group) was prepared as described. A running buffer as described by Swedberg was prepared (0.25M ammonium phosphate) with pH of 6.0 and 7.0. The column length and applied voltage utilized were in accordance with the aforementioned Beckman high performance capillary zone electrophoresis instrument (25 μm × 25 cm capillary; 400v/cm; 78 μa; 200 nm absorbance).

An electropherogram of the separation of Set A proteins is set forth in FIG. 28, using the described buffer at pH 6.0. Separations were well defined over an approximate 40 minute period. At pH 7.0, only Set A proteins 1 and 2 were observed in the electropherogram of FIG. 29 (the remaining proteins may have been either adsorbed, or the peaks thereof were defined well after the 40 min analytical run time). Attempts at separating serum protein using the conditions as set forth in FIGS. 28 and 29 were investigated. Separation of serum proteins was not evident of either pH 6.0 or 7.0 using the aforementioned buffer in conjunction with the described coated column as evidenced by the resulting electropherogram of FIGS. 30 and 31, respectively.

The results of Example VII indicate that while particular conditions may evidence successful separation of purified, well defined proteins, such conditions may not evidence applicability to non-model proteins such as, e.g., serum proteins.

The above examples are of preferred embodiments of the disclosed invention. Modifications that are within the purview of those skilled in the art are intended to be within the scope of the invention.

What is claimed is:

1. A capillary zone electrophoresis method for the analysis of sample constituents to be separated comprising the steps of:
   a) introducing a solution comprising said sample constituents into an untreated capillary tube including therein a dynamic coating buffer, said dynamic coating buffer comprising at least one agent having at least two dissociation constants, wherein the molarity of said agent is between about 0.2M and about 1.0M and the pH of said buffer is between about 3.0 and about 11.0;
   b) applying an electric charge to said capillary of sufficient voltage to cause the constituents to be separated from each other; and
   c) detecting the constituents of said sample.

2. The method of claim 1 wherein the internal diameter of said capillary tube is between about 5 microns and about 2000 microns.

3. The method of claim 1 wherein the internal diameter of said capillary tube is between about 20 microns and 25 microns.

4. The method of claim 1 wherein the agent is selected from the group consisting of phosphoric acid, alkali-metal phosphates having at least one proton, mono-, di-, tri-, and tetra-alkyl ammonium phosphate having from about 1 to about 8 carbon atoms, alkyl phosphate having from about 1 to about 20 carbon atoms, carbonic acid, alkali-metal carbonates having at least one proton, mono-, di-, tri-, and tetra-alkyl ammonium carbonate having from about 1 to about 8 carbon atoms, and alkyl carbonate having from about 1 to about 20 carbon atoms.

5. The method of claim 1 wherein the agent is an alkali-metal phosphate.

6. The method of claim 1 wherein the agent is sodium phosphate.

7. The method of claim 6 wherein the molarity of said sodium phosphate in said buffer is about 0.5M.

8. The method of claim 1 wherein the buffer further comprising at least one constituent selected from the group consisting of acetic acid, 2-(N-morpholino) ethanesulfonic acid, 3-(N-morpholino) proponesulfonic acid, N-[tris-hydroxymethyl) ethyl] glycine, tris-(hydroxymethyl) aminomethane, cyclohexyl aminoethane - sulfonic acid, triethyl amine, dimethyl amine, the alkyl amides having up to about 12 carbon atoms, N-2-hydroxyethyl piperazine-N'-3-propane sulfonic acid, piperazine-N, N'-bis (2-ethanesulfonic acid), 3-{[tris-(hydroxynethyl) methyl] amino} propanesulfonic acid, 2-{[(hydroxymethyl)methyl] amino} ethanesulfonic acid, and urea.

9. The method of claim 1 wherein the sample comprises at least one proteinaceous constituent.

10. A capillary zone electrophoresis method for the analysis of sample constituents to be separated comprising the steps of:
   a) introducing a solution comprising said sample constituents and a dynamic coating buffer into an untreated capillary tube, said dynamic coating buffer comprising at least one agent having at least two dissociation constants, wherein the molarity of said agent is between about 0.2M and about 1.0M and the pH of said buffer is between about 3.0 and about 11.0;
   b) applying an electric charge to said capillary of sufficient voltage to cause the constituents to be separated from each other; and
   c) detecting the constituents of said sample.

* * * * *